United States Patent [19]

Gerster

[11] Patent Number: 4,689,338

[45] Date of Patent: Aug. 25, 1987

[54] 1H-IMIDAZO[4,5-C]QUINOLIN-4-AMINES AND ANTIVIRAL USE

[75] Inventor: John F. Gerster, Woodbury, Minn.

[73] Assignee: Riker Laboratories, Inc., St. Paul, Minn.

[21] Appl. No.: 798,385

[22] Filed: Nov. 15, 1985

Related U.S. Application Data

[63] Continuation-in-part of Ser. No. 553,158, Nov. 18, 1983, abandoned.

[51] Int. Cl.[4] .................. C07D 471/04; A61K 31/47
[52] U.S. Cl. ..................... 514/293; 546/82; 546/159
[58] Field of Search .......................... 546/82; 514/293

[56] References Cited

U.S. PATENT DOCUMENTS

| | | | |
|---|---|---|---|
| 3,700,674 | 10/1972 | Diehl et al. | 546/307 |
| 4,013,665 | 3/1977 | Crenshaw et al. | 546/82 |
| 4,052,393 | 10/1977 | Treuner | 260/250 |
| 4,191,767 | 3/1980 | Warner et al. | 424/250 |
| 4,197,403 | 4/1980 | Warner et al. | 544/346 |

FOREIGN PATENT DOCUMENTS

| | | |
|---|---|---|
| 0107455 | 5/1984 | European Pat. Off. |
| 0187705 | 7/1986 | European Pat. Off. |
| 2103 | 6/1983 | Hungary |
| 76045 | 12/1982 | Portugal |

OTHER PUBLICATIONS

Backeberg et al., J. Chem. Soc., 972–977 (1938).
Backeberg, et al., J. Chem. Soc., 1083–1089 (1938).
Bachman, et al., J. Org. Chem. 15, 1278–1284 (1950).
Surrey et al., J. Am. Chem. Soc., 73, 2413 (1951).
Jain, et al., J. Med. Chem. 11, pp. 87–92 (1968).
Baranov et al., Chem. Abs. 85, 94362 (1976).
Abbasi et al., Monatsh. Chem. 111 (4), pp. 963–969 (1980).
Berenyi et al., J. Heterocyclic Chem. 18, 1537–1540 (1981).
Derwent Abstract for Hungarian Application No. 2103/83.
Derwent Abstract for Portuguese Application No. 76045.
Koenigs and Freund, Chemische Berichte, 80, 143 (1947).
Quinolines, pp. 562,563, Part 1, from The Chemistry of Heterocyclic Compounds, Weissberger and Taylor (1977).

Primary Examiner—Henry R. Jiles
Assistant Examiner—Dale A. Bjorkman
Attorney, Agent, or Firm—Donald M. Sell; James A. Smith; Robert W. Sprague

[57] ABSTRACT

1H-Imidazo[4,5-c]quinolin-4-amines which are antivirals. Pharmacological methods of using such compounds and pharmaceutical compositions containing such compounds are also described.

22 Claims, No Drawings

1H-IMIDAZO[4,5-C]QUINOLIN-4-AMINES AND ANTIVIRAL USE

CROSS-REFERENCE TO RELATED APPLICATION

This application is a continuation-in-part of copending application U.S. Ser. No. 553,158, filed November 18, 1983, abandoned.

TECHNICAL FIELD

This invention relates to substituted 1H-imidazo[4,5c-]quinoline compounds. Pharmacological methods of using such compounds and pharmaceutical compositions containing such compounds are also included within the scope of the invention.

BACKGROUND OF THE INVENTION

The earliest report of an imidazo[4,5-c]quinoline ring system was by Backeberg et al., J. Chem. Soc., 972–977 (1938). However, his report of 4-methyl-1H-imidazo[4,5-c]quinoline and 2,4-dimethyl-1H-imidazo[4,5-c]quinoline (named as 2-methylquin(3:4:5': 4')iminazole and 2:2'-dimethylquin(3:4:5':4')iminazole) is known to be erroneous in view of later work of Koenigs and Freund, Chemische Berichte 80, 143 (1947).

A further report by Backeberg, J. Chem. Soc., 1083–1089 (1938) of 2,4-dimethyl-3-phenyl-3H-imidazo[4,5-c]quinoline (named 1'-phenyl-2:2'-dimethylquin(3:4:5':4')iminazole) is also known to be erroneous in view of the above work of Koenigs and Freund.

The first reliable report of a 1H-imidazo[4,5-c]-quinoline is by Bachman et al., J. Org. Chem. 15, 1278–1284 (1950) who synthesized 1-(6-methoxy-8-quinolinyl)-2-methyl-1H-imidazo[4,5-c]quinoline as a possible antimalarial agent.

Surrey et al, J. Am. Chem. Soc. 73, 2413 (1951) synthesized certain 3-nitro- and 3-amino-4-dialkylaminoalkylaminoquinolines as possible antimalarial and antibacterial agents.

Jain et al., J. Med. Chem. 11, pp. 87–92 (1968), synthesized the compound 1-[2-(4-piperidyl)ethyl]-1H-imidazo[4,5-c]quinoline as a possible anticonvulsant and cardiovascular agent.

Baranov et al., Chem Abs. 85, 94362 (1976), reported several 2-oxoimidazo[4,5-c]quinolines.

Abbasi et al., Monatsh. Chem. 111 (4), pp. 963–969 (1980), reported certain 2H-3-hydroxyimidazo[4,5-c]quinolines.

Berenyi et al., J. Heterocyclic Chem. 18, 1537–1540 (1981), reported certain 2-oxoimidazo[4,5-c]-quinolines.

U.S. Patent No. 3,700,674 (Diehl et al) describes certain 4-alkylamino-3-nitroquinolines as herbicidal compounds.

DETAILED DESCRIPTION OF THE INVENTION

This invention relates to substituted 1H-imidazo[4,5-c]quinoline compounds which exhibit antiviral activity. This invention also relates to pharmacological methods of using such compounds and pharmaceutical compositions containing such compounds.

More specifically, this invention relates to novel compounds of Formula I

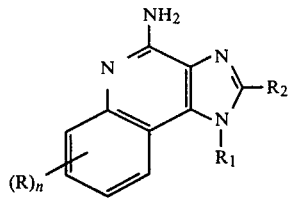

wherein $R_1$ is selected from the group consisting of alkyl of one to about ten carbon atoms, hydroxyalkyl of one to about six carbon atoms, acyloxyalkyl wherein the acyloxy moiety is alkanoyloxy of two to about four carbon atoms or benzoyloxy, and the alkyl moiety contains one to about six carbon atoms, benzyl, (phenyl)ethyl or phenyl, the benzyl, (phenyl)ethyl or phenyl substituent being optionally substituted on the benzene ring by one or two moieties independently selected from the group consisting of alkyl of one to about four carbon atoms, alkoxy of one to about four carbon atoms and halogen, with the proviso that if said benzene ring is substituted by two of said moieties, then said moieties together contain no more than 6 carbon atoms; $R_2$ is selected from the group consisting of hydrogen, alkyl of one to about eight carbon atoms, benzyl, (phenyl)ethyl and phenyl, the benzyl, (phenyl)ethyl or phenyl substituent being optionally substituted on the benzene ring by one or two moieties independently selected from the group consisting of alkyl of one to about four carbon atoms, alkoxy of one to about four carbon atoms and halogen, with the proviso that when the benzene ring is substituted by two of said moieties, then the moieties together contain no more than 6 carbon atoms; and each R is independently selected from the group consisting of alkoxy of one to about four carbon atoms, alkyl of one to about four carbon atoms and halogen, and n is an integer from 0 to 2, with the proviso that if n is 2, then said groups together contain no more than 6 carbon atoms; and pharmaceutically acceptable addition salts thereof.

The compounds of Formula I may be used in the form of acid addition salts such as hydrochlorides, dihydrogen sulfates, trihydrogen phosphates, hydrogen nitrates, methane sulfonates and salts of other pharmaceutically acceptable acids. Pharmaceutically acceptable acid-addition salts of compounds of Formula I are generally prepared by reaction of the respective compound with an equimolar amount of a relatively strong acid, preferably an inorganic acid such as hydrochloric, sulfuric or phosphoric acid or an organic acid such as methanesulfonic acid in a polar solvent. Isolation of the salt is facilitated by the addition of a solvent in which the salt is insoluble, an example of such a solvent being diethyl ether.

Generally, alkyl moieties which may be contained in the compounds of the invention may be straight or branched-chain or cyclic.

$R_1$ substituents which are alkyl preferably contain one to about eight carbon atoms, and more preferably contain about four to about six carbon atoms.

$R_2$ substituents which are alkyl preferably contain one to about four carbon atoms.

Hydroxyalkyl substituents which may be contained in the compounds of the invention preferably contain one to about four carbon atoms.

The remaining substituents which may be contained in the compounds of the invention and contain an alkyl radical such as in the case of the substituents alkoxy and alkyl (other than $R_1$ and $R_2$ as alkyl) preferably contain one or two carbon atoms in each alkyl radical.

The preferred cyclic alkyl substituents contain six or seven carbon atoms.

The halogen substituents which may be contained in the compounds of the instant invention are selected from fluorine, chlorine and bromine. Preferred halogen substituents are fluorine and chlorine.

When R is alkoxy it is preferably methoxy.

It is preferred that n of Formula I be zero or one. It is most preferred that n of Formula I be zero.

If $R_1$ is substituted benzyl, (phenyl)ethyl or phenyl, it is preferred that the benzene ring be monosubstituted. It is most preferred that the benzyl, (phenyl)ethyl or phenyl substituent be unsubstituted. As used in the instant specification and claims, "(phenyl)ethyl" denotes 1-(phenyl)ethyl or 2-(phenyl)ethyl.

It is presently preferred that $R_1$ be alkyl, benzyl, cyclohexylmethyl or hydroxyalkyl.

When $R_1$ is hydroxyalkyl, the compounds of the invention may contain one to three hydroxy substituents. Preferred hydroxyalkyl groups contain one or two hydroxy substituents.

Presently preferred compounds are:
1-methyl-1H-imidazo[4,5-c]quinolin-4-amine;
1,2,8-trimethyl-1H-imidazo[4,5-c]quinolin-4-amine;
1-(2-hydroxyethyl)-1H-imidazo[4,5-c]quinolin-4-amine;
1-benzyl-1H-imidazo[4,5-c]quinolin-4-amine;
1,2-dimethyl-1H-imidazo[4,5-c]quinolin-4-amine;
1-benzyl-2-methyl-1H-imidazo[4,5-c]quinolin-4-amine;
1,8-dimethyl-1H-imidazo[4,5-c]quinolin-4-amine;
1-cyclohexylmethyl-1H-imidazo[4,5-c]quinolin-4-amine;
1-(2,3-dihydroxypropyl)-1H-imidazo[4,5-c]quinolin-4-amine;
1-n-hexyl-2-methyl-1H-imidazo[4,5-c]quinolin-4-amine;
1-n-butyl-1H-imidazo[4,5-c]quinolin-4-amine;
1,2-diisobutyl-1H-imidazo[4,5-c]quinolin-4-amine;
1-n-hexyl-1H-imidazo[4,5-c]quinolin-4-amine;
1-(2-hydroxy-2-methylpropyl)-1H-imidazo-[4,5-c]quinolin-4-amine; and
1-isobutyl-1H-imidazo[4,5-c]quinolin-4-amine.

The presently most preferred compound is the last one mentioned above.

The compounds of the invention of Formula I are prepared as described in the Reaction Scheme illustrated below, wherein R, R1, R2 and n are as defined above:

Reaction Scheme

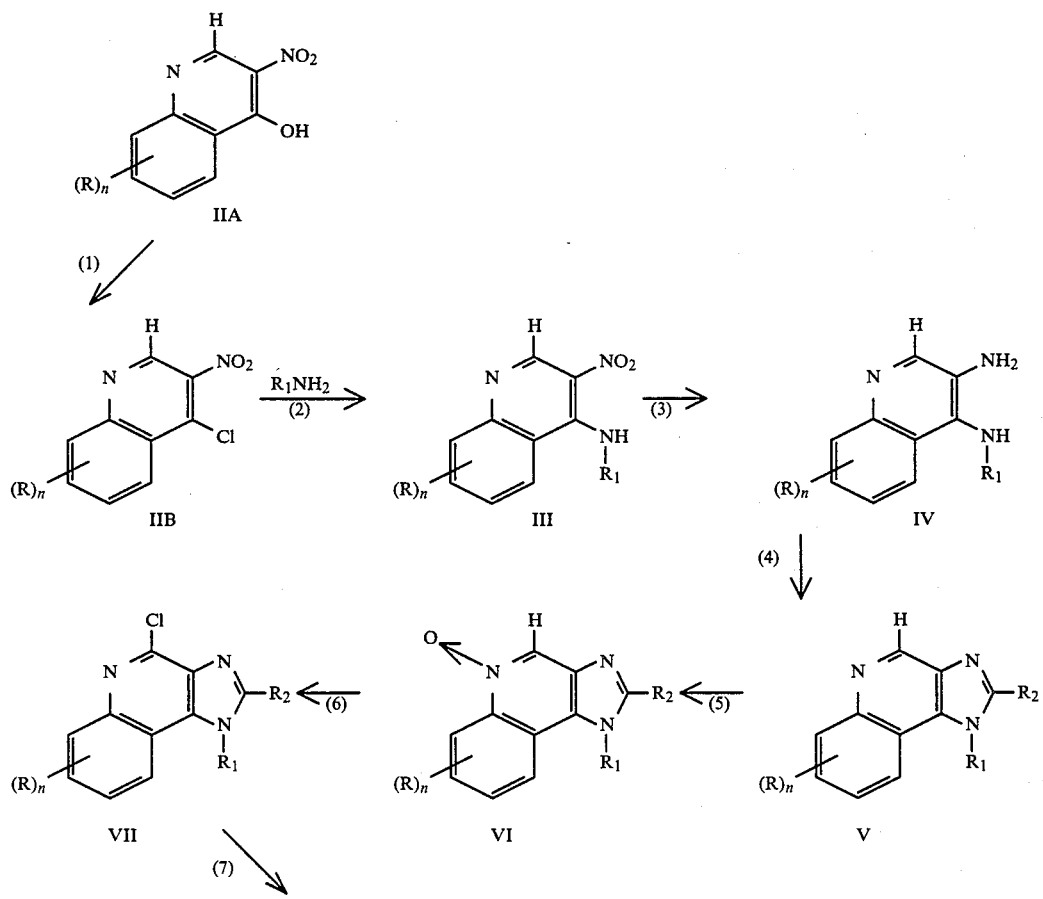

-continued
Reaction Scheme

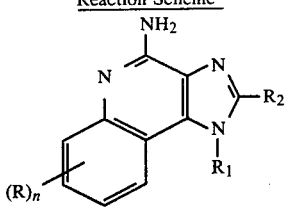

I

Many quinolines of Formula IIB are known compounds (see, for example, U.S. Pat. No. 3,700,674 and references cited therein). Those which are not may be prepared by know methods, for example, from 4-hydroxy-3-nitroquinolines as illustrated in step (1) of the Reaction Scheme. Step (1) may be conducted by reacting the 4-hydroxy-3-nitroquinoline of Formula IIA with phosphorus oxychloride. The reaction is preferably conducted in N,N-dimethylformamide and is accompanied by heating. A large molar excess of phosphorus oxychloride is preferably avoided. Employment of about a 1–2 molar ratio of phosphorus oxychloride to the 4-hydroxy-3-nitroquinoline has been found to be particularly suitable.

In step (2) an optionally substituted 3-nitro-4-chloroquinoline of Formula IIB is reacted by heating with an amine of the formula $R_1NH_2$ in a suitable solvent such as water or tetrahydrofuran to provide a quinoline of Formula III. Compounds of Formula III wherein $R_1$ is cyclohexylmethyl or hydroxyalkyl are novel.

Steps (1) and (2) may be combined such that the 3-nitro-4-chloroquinoline need not be isolated prior to reacting with the amine. Such a reaction is exemplified in Example 134 and Example 188 (Step A) below.

Compounds of Formula III are catalytically reduced in step (3) using a platinum catalyst such as platinum on charcoal to provide compounds of Formula IV. The reduction is conveniently carried out on a Parr apparatus in a non-reactive solvent such as toluene or a lower alkanol. Compounds of Formula IV wherein $R_1$ is cyclohexylmethyl or hydroxyalkyl are novel.

In step (4) the intermediate compounds of Formula Iv are generally reacted with a 1,1-dialkoxyalkyl alkanoate such as diethoxymethyl acetate, or a carboxylic acid which will introduce the desired $R_2$ group, or a trialkyl ortho ester of the formula $R_2C(Oalkyl)_3$, wherein "alkyl" is an alkyl group containing 1 to about 4 carbon atoms, or the combination of such a carboxylic acid with such a trialkyl ortho ester to provide a novel compound of Formula V. The compounds of Formula V are particularly useful as intermediates because the 4-position is unsubstituted. The reaction of step (4) is carried out by heating, e.g., at about 130° C., in the presence of an acid, preferably an alkanoic acid having one more carbon atom than $R_2$.

When $R_2$ is phenyl, the intermediate compounds of Formula IV are reacted with benzaldehyde or a substituted-benzaldehyde and then dehydrogenated by heating in an inert solvent in the presence of palladium on carbon to provide a compound of Formula V.

Step (5) provides a novel intermediate of Formula VI through oxidation of the compound of Formula V with a conventional oxidizing agent which is capable of forming N-oxides. Suitable oxidizing agents include peracids and hydrogen peroxide. The oxidation reaction is preferably conducted in glacial acetic acid. Heating is generally employed to accelerate the rate of reaction.

Steps (4) and (5) may be combined such that the compound of Formula V need not be isolated prior to reaction with the oxidizing agent. Such a reaction is exemplified in Example 188 (Step C) below.

In step (6) the N-oxide of Formula VI is converted to the 4-chloro intermediate of Formula VII by heating in the presence of a suitable chlorinating agent such as phosphorus oxychloride. It is preferred that phosphorus oxychloride be used in combination with N,N-dimethylformamide as the solvent.

In step (7) the 4-chloro group is replaced by a 4-amino group to provide a compound of the invention of Formula I. The reaction is carried out in the presence of ammonium hydroxide or, preferably, ammonia. The intermediate of Formula VII is generally heated at 125 to 175° C. under pressure for 4–24 hours. It is preferred that the reaction be conducted in a sealed reactor in the presence of either ammonium hydroxide or a solution of ammonia in an alcohol, such as, 15% ammonia in methanol.

For compounds wherein $R_1$ is hydroxyalkyl, the synthesis illustrated in the Reaction Scheme above is preferably modified. Specifically, it is generally necessary to block or protect the hydroxy group, for example, with an acyloxy group such as alkanoyloxy or benzoyloxy for step(s) (5) and/or (6) and/or (7), and then to remove the blocking group. Such blocking reactions are exemplified in Examples 115-123 below.

The compounds of the invention exhibit antiviral activity in mammals and can thus be used to control viral infections. A preferred use of the compounds of the invention is as agents to control infections caused by Herpes simplex virus, Type I or Type II.

The anti-Herpes activity of the compounds of Formula I relative to primary lesions caused by Herpes simplex virus (either Type I or Type II) is preferably demonstrated using the method described generally by Kern, et al., Antimicrob. Agents Chemother. 14, 817-823 (1978).

This method uses female guinea pigs of 200 to 300 grams in weight, preferably 200 to 250 grams in weight. The preferred strain of guinea pigs is Hartley. The guinea pigs are anesthetized with pentobarbital or methoxyflurane, and are then infected with about $10_5$ plaque forming units of Herpes simplex virus, either type I or type II, intravaginally using a cotton swab. The compounds of Formula I are formulated in saline or water using a surfactant such as "Tween 80" (a polyoxyethylene sorbitan monooleate, commercially available from Emulsion Engineering Inc., Elk Grove Village, Ill.). Alternatively, the compounds of Formula I may be formulated in "PEG 400" (a polyethyleneglycol of average molecular weight of about 400, commercially available from Union Carbide Corporation), or in a polyethyleneglycol cream. The drugs are applied topically (e.g., intravaginally or cutaneously), for example, twice daily for a predetermined number of days, for example, five days. Application is initiated at a predetermined interval before or after infection such as one hour after infection. Virus replication can be monitored by determining the amount of virus recovered with vaginal swabs taken, for example, on days 1, 2, 3, 5 or 7 after infection. Virus is eluted from the swab in 1 ml of cell growth medium (Medium 199, Gibco Laboratories, Grand Island, New York) and virus titer is determined using cell monolayers. External lesions are scored daily for 10 days using the following scale: zero, no lesion; 1, redness or swelling; 2, a few small vesicles; 3, several large vesicles; 4, large ulcers and necrosis; 5, paralysis. Percent inhibition of lesion development is determined by comparing untreated, but infected control animals and drug treated animals. Comparison studies with known drugs such as phosphonacetic acid and acyclovir may also be conducted. The compounds of the invention inhibit lesion development in that they reduce the number of lesions and the severity thereof. It has been found that the compound 1-isobutyl-1H-imidazo[4,5-c]quinolin-4-amine is efficacious when administered to guinea pigs beginning as earlier as 7 days before infection or as late as 72 hours after infection.

The compound 1-isobutyl-1H-imidazo[4,5-c]-quinolin-4-amine of the invention not only exhibits activity against primary lesions, but exhibits activity against recurrent lesions as well. Such activity may be demonstrated using the method described by Stanberry, et al., Journal of Infectious Diseases, 146, 397–404 (1982). Guinea pigs treated with a suspension of 1.0% of the compound in a 5% "Tween 80" water solution were found to experience fewer episodes of recurrent lesions and recurrent lesions lasted for fewer days than in the case of controls. In the foregoing study, the compound was administered topically to the lesions every 12 hours for 21 days beginning 41 days after intravaginal inoculation with Herpes simplex virus Type II. It is believed that other compounds of the invention would exhibit activity against recurrent lesions as well.

In the preferred antiviral method of the invention the compounds of Formula I are used to control Type I or Type II Herpes simplex virus by applying to a population thereof an amount of a compound of Formula I sufficient to attain said control.

The method of the invention is preferably used in vivo for treating infections caused by the viruses, especially in mammals. The method is generally effective when a compound of Formula I or a formulation thereof is administered topically (e.g., intravaginally or on the skin), for example, to a genital herpes infection. The compounds of Formula I may also be used to treat a genital herpes infection by oral administration. Compounds of Formula I are also generally active against herpes infections by intraperitoneal administration. The preferred route of administration is topical.

It has also been found that several compounds of the invention including 1-isobutyl-1H-imidazo[4,5-c]-quinolin-4-amine and 4-amino-1-(2-hydroxy-2-methylpropyl)-1H-imidazo[4,5-c]quinoline (a metabolite of 1-isobutyl-1H-imidazo-[4,5-c]quinolin-4-amine in the guinea pig) induce the biosynthesis of interferon in the guinea pig following a single intravaginal or oral dose of the antiviral compound, and hence the compound is an immunomodulator. The assay employed was that described in Green et al., J. Clin. Microbiology, 12 (3), 433–438 (1980) and Overall et al, J. Interferon Research 4, 529–533 (1984), both incorporated herein by reference, except that guinea pig fibroblasts were used as the cell system and EMC or mengovirus was used as the infecting virus (see Example 198) in evaluating the compounds of the invention. As shown in Example 199, induction of interferon was also observed in the monkey in response to 1-isobutyl-1H-imidazo[4,5-c]quinoline.

While not wishing to be bound to any mechanism, it is believed that the antiviral activity exhibited by the compounds of the invention is attributable to immunomodulation including interferon induction, and it is believed that all compounds of the invention would induce interferon. Further, the fact that interferon is induced suggests that the compounds of the invention could be useful in treating other disease states such as rheumatoid arthritis, warts, eczema, and cancer.

Compounds of the invention are formulated for the various routes of administration in known, pharmaceuticallY accepted vehicles such as water or polyethylene glycol. Suitable formulations for topical application will generally contain less than 10% by weight of a compound of Formula I, and will preferably contain about 0.1% to 5% by weight of a compound of Formula I.

The compounds of the invention are preferably administered in water which contains either a surfactant such as the "Tween 80" discussed above or cellulose. A 5% concentration of the surfactant has been found to be generally useful in topical, oral and intraperitoneal formualations. The presently preferred antiviral formulation for topical administration is a cream containing 1% by weight of the preferred antiviral compound 1-isobutyl-1H-imidazo[4,5-c]quinolin-4-amine in micronized form (i.e., particle size of 1-2 microns in diameter); 0.2% by weight of methyl paraben; 0.02% by weight of propyl paraben; 5% by weight of "Avicel CL-611" (a colloidal form of microcrystalline cellulose which has been coprocessed with sodium carboxymethyl cellulose (available from FMC Corporation, Philadelphia, Pennsylvania); and 93.78% by weight of water. The formulation is prepared by dry-mixing the antiviral compound with the "Avicel CL-611", and then combining that mixture with a solution containing the methyl paraben and propyl paraben in the water.

The following examples are provided to illustrate the invention and are not intended to be limiting thereof.

EXAMPLE 1

Preparation of a Compound of Formula III

To a stirred solution of 50.0g (0.24 mole) of 4-chloro-3-nitroquinoline in 300 ml of tetrahydrofuran was added, in small portions, 52.7g (0.72 mole) of isobutylamine. The mixture was heated at its reflux temperature for one hour, and was then evaporated in vacuo. Water was added to the residue and the solid was separated by filtration. The solid was suspended in one liter of water, and was dissolved by the gradual addition of concentrated hydrochloric acid (to pH 3 to 4), at which time the solution was filtered. The filtrate was basified (to pH 9 to 10) by the addition of concentrated ammonium hydroxide to provide bright yellow 4-(isobutylamino)-3-nitroquinoline, m.p. 119°–121° C. The structural assignment was supported by infrared spectral analysis.

EXAMPLE 2

Alternative Preparation of a Compound of Formula III

To a stirred solution of 40% aqueous methylamine was added, in small portions, 30.0g (0.144 mole) of 4-chloro-3-nitroquinoline. The reaction mixture was heated at its reflux temperature for about 0.75 hour. After cooling, the mixture was poured into 300 ml of water. The solid was separated by filtration, and was then suspended in 300 ml of water. Acidification with 6N hydrochloric acid to pH 3 to 4 effected dissolution of most of the solid. Filtration was followed by basification of the filtrate with concentrated ammonium hydroxide to pH 8 to 10 to provide a yellow precipitate. The solid was separated by filtration, washed with water, and recrystallized from ethanol to provide yellow 4-methylamino-3-nitroquinoline, m.p. 168–170° C. Analysis: Calculated for $C_{10}H_9N_3O_2$ %C, 59.1; %H, 4.5: %N, 20.7: Found: %C, 59.0; %H, 4.2; %N, 20.8.

Using the methods of Examples 1 and 2 and starting with indicated substituted quinolines and primary amines, the following compounds of Formula III were prepared (Table I):

TABLE I

| Ex. No. | Quinoline Starting Material of Formula IIB | Primary Amine Starting Material | Intermediate of Formula III (m.p. in °C.) |
|---|---|---|---|
| 3 | 4,6-dichloro-3-nitroquinoline | methylamine | 6-chloro-4-methylamino-3-nitroquinoline (not taken) |
| 4 | 4-chloro-3-nitroquinoline | ethanolamine | 4-(2-hydroxyethylamino)-3-nitroquinoline (204–207) |
| 5 | 4-chloro-3-nitroquinoline | 2,3-dihydroxypropylamine | 4-(2,3-dihydroxypropylamino)-3-nitroquinoline (209–211) |
| 6 | 4-chloro-3-nitroquinoline | ethylamine | 4-ethylamino-3-nitroquinoline (145–148) |
| 7 | 4-chloro-6-methyl-3-nitroquinoline | methylamine | 6-methyl-4-methylamino-3-nitroquinoline (168–171) |
| 8 | 4-chloro-6-methyl-3-nitroquinoline | isobutylamine | 4-isobutylamino-6-methyl-3-nitroquinoline (108–110) |
| 9 | 4-chloro-6-fluoro-3-nitroquinoline | methylamine | 6-fluoro-4-methylamino-3-nitroquinoline (198–202) |
| 10 | 4,7-dichloro-3-nitroquinoline | isobutylamine | 7-chloro-4-isobutylamino-3-nitroquinoline (not taken) |
| 11 | 4-chloro-3-nitroquinoline | aniline | 3-nitro-4-phenylaminoquinoline (129–132) |
| 12 | 4-chloro-3-nitroquinoline | 4-methoxyaniline | 4-(4-methoxyphenylamino)-3-nitroquinoline (136–138) |
| 13 | 4-chloro-3-nitroquinoline | 4-fluoroaniline | 4-(4-fluorophenylamino)-3-nitroquinoline (147–151) |
| 14 | 4-chloro-3-nitroquinoline | n-butylamine | 4-(n-butylamino)-3-nitroquinoline (81–83) |
| 15 | 4-chloro-3-nitroquinoline | 3-hydroxypropylamine | 4-(3-hydroxypropylamino)-3-nitroquinoline (159–162) |

EXAMPLE 16

Preparation of a Compound of Formula IV

To a slolution of 57.3g (0.23 mole) of 4-isobutylamino-3-nitroquinoline (from Example 1) in 600 ml of ethanol was added about 2 g of platinum on charcoal, and the mixture was hydrogenated on a Parr apparatus for three hours. Filtration followed by evaporation in vacuo Provided a residue which gradually solidified to yellow solid 3-amino-4-(isobutylamino) quinoline.

Using the method of Example 16, the intermediates of Formula IV shown in Table II were prepared. In those cases where the hydrochloride is listed, it was obtained by first bubbling hydrogen chloride through an ethanol solution of the free amine, and then separation the solid product by filtration.

TABLE II

| Ex. No. | Starting Material of Formula III (Example No.) | Product of Formula IV (m.p. in °C.) |
|---|---|---|
| 17 | 2 | 3-amino-4-(methylamino)quinoline hydrochloride (294–296) |
| 18 | 3 | 3-amino-6-chloro-4-(methylamino)quinoline (not taken) |
| 19 | 4 | 3-amino-4-(2-hydroxyethylamino)quinoline dihydrochloride (282–283) |
| 20 | 5 | 3-amino-4-(2,3-dihydroxypropylamino)quinoline hydrochloride (201–204) |
| 21 | 6 | 3-amino-4-(ethylamino)quinoline hydrochloride (226–229) |
| 22 | 7 | 3-amino-6-methyl-4-(methylamino)quinoline hydrochloride (>300) |
| 23 | 8 | 3-amino-4-isobutylamino-6-methylquinoline (not taken) |
| 24 | 9 | 3-amino-6-fluoro-4-(methylamino)quinoline (not taken) |
| 25 | 10 | 3-amino-7-chloro-4-(isobutylamino)quinoline (not taken) |
| 26 | 11 | 3-amino-4-phenylaminoquinoline (not taken) |
| 27 | 12 | 3-amino-4-(4-methoxyphenylamino)quinoline (not taken) |
| 28 | 13 | 3-amino-4-(4-fluorophenylamino)quinoline (not taken) |
| 29 | 14 | 3-amino-4-(n-butylamino)quinoline (not taken) |
| 30 | 15 | 3-amino-4-(3-hydroxypropylamino)quinoline (not taken) |

EXAMPLE 31

Preparation of a Compound of Formula V

A crude reaction product obtained by the method of Example 2 of 0.207 mole of 3-amino-4-(methylamino)-quinoline was mixed with 500 ml of glacial acetic acid and 76 ml of triethyl orthoacetate, and the resulting mixture was heated at reflux for two hours. Evaporation provided a residue which was dissolved in 800 ml of water. The solution was basified with concentrated ammonium hydroxide. The solid was separated by filtration and washed with water to provide 1,2-dimethyl-1H-imidazo[4,5-c]quinoline. When a sample of this product was recrystallized from diethyl ether it had a melting point of 194°–196° C. Analysis: Calculated for $C_{12}H_{11}N_3$: %C, 73.1; %H, 5.6; %N, 21.3; Found: %C, 73.4; %H, 5.7; %N, 21.5.

Using the method of Example 31 and the indicated carboxylic acids and trialkyl orthoesters, the intermediates of Formula V shown in Table III were prepared.

TABLE III

| Ex. No. | Intermediate of Formula IV (Example No.) | Ortho Ester; Carboxylic Acid | Intermediate of Formula V (m.p. in °C.) |
|---|---|---|---|
| 32 | 16 | triethyl orthoformate; formic acid | 1-isobutyl-1H—imidazo[4,5-c]quinoline (92–95) |
| 33 | 18 | triethyl orthoacetate; acetic acid | 8-chloro-1,2-dimethyl-1H—imidazo[4,5-c]quinoline (not taken) |

TABLE III-continued

| Ex. No. | Intermediate of Formula IV (Example No.) | Ortho Ester; Carboxylic Acid | Intermediate of Formula V (m.p. in °C.) |
|---|---|---|---|
| 34 | 19 | triethyl orthoformate; formic acid | 1-(2-hydroxyethyl)-1H—imidazo[4,5-c]quinoline (170–172) |
| 35 | 20 | triethyl orthoacetate; acetic acid | 1-(2,3-dihydroxypropyl)-2-methyl-1H—imidazo[4,5-c]-quinoline (232–234) |
| 36 | 21 | triethyl orthoacetate; acetic acid | 1-ethyl-2-methyl-1H—imidazo[4,5-c]quinoline (126–129) |
| 37 | 22 | triethyl orthoformate; formic acid | 1,8-dimethyl-1H—imidazo-[4,5-c]quinoline hydrate (180–184) |
| 38 | 22 | triethyl orthoacetate; acetic acid | 1,2,8-trimethyl-1H—imidazo-[4,5-c]quinoline (220–221) |
| 39 | 21 | triethyl orthoformate; formic acid | 1-ethyl-1H—imidazo[4,5-c]-quinoline (80–82) |
| 40 | 23 | triethyl orthoformate; formic acid | 1-isobutyl-8-methyl-1H—imidazo[4,5-c]quinoline (160–163) |
| 41 | 24 | triethyl orthoformate; formic acid | 8-fluoro-1-methyl-1H—imidazo[4,5-c]quinoline hydrate (201–205) |
| 42 | 25 | triethyl orthoformate; formic acid | 7-chloro-1-isobutyl-1H—imidazo[4,5-c]quinoline (not taken) |
| 43 | 26 | triethyl orthoformate; formic acid | 1-phenyl-1H—imidazo-[4,5-c]quinoline (137–139) |
| 44 | 27 | triethyl orthoformate; formic acid | 1-(4-methoxyphenyl)-1H—imidazo[4,5-c]quinoline (150–152) |
| 45 | 28 | triethyl orthoacetate; acetic acid | 1-(4-fluorophenyl)-2-methyl-1H—imidazo-[4,5-c]quinoline (191–193) |
| 46 | 27 | triethyl orthoacetate; acetic acid | 1-(4-methoxyphenyl)-2-methyl-1H—imidazo[4,5-c]quinoline (174–176) |
| 47 | 28 | triethyl orthoformate; formic acid | 1-(4-fluorophenyl)-1H—imidazo[4,5-c]quinoline (159–161) |
| 48 | 29 | triethyl orthoformate; formic acid | 1-(n-butyl)-1H—imidazo-[4,5-c]quinoline (not taken) |
| 49 | 30 | triethyl orthoformate; formic acid | 1-(3-hydroxypropyl)-1H—imidazo[4,5-c]quinoline (not taken) |
| 50 | 17 | triethyl orthoformate; formic acid | 1-methyl-1H—imidazo-[4,5-c]quinoline (143–145) |
| 51 | 20 | triethyl orthoformate; formic acid | 1-(2,3-dihydroxypropyl)-1H—imidazo[4,5-c]quinoline (228–230) |
| 52 | 16 | triethyl orthoacetate; acetic acid | 1-isobutyl-2-methyl-1H—imidazo[4,5-c]quinoline hydrate (85–88) |
| 53 | 24 | triethyl orthoacetate; acetic acid | 1,2-dimethyl-8-fluoro-1H—imidazo[4,5-c]quinoline (234–239) |

EXAMPLE 54

Preparation of a Compound of Formula VI.

To a solution of 9.3g (0.0413 mole) of 1-isobutyl-1H-imidazo [4,5-c]quinoline (from Example 32) in 150 ml of acetic acid was added 1.5 equivalents (0.062 mole) of 30% hydrogen peroxide. The mixture was heat at 65°–70° C. for one day, and was then evaporated. The residue was neutralized with saturated sodium bicarbonate solution, and the resulitng mixture was extracted with dichloromethane. The extracts were dried, and were then evaporated to provide a residue which solidifed gradually to yellow solid 1-isobutyl-1H-imdazo [4,5-c]quinolin-5-oxide. This product was recrystallized twice from ethyl acetate to give a green solid, m.p. 211°–213° C. Analysis: calculated for $C_{14}H_{15}N_3O$: %C, 69.7; %7; %H, 6.3; %N, 17.4; Found %C, 69,7; %H, 6.3; %N, 17.1.

Using the method of Example 54 intermediate compounds of Formula VI show in Table IV were prepared.

TABLE IV

| Ex. No. | Intermediate of Example V (Example No.) | Intermediate of Formula VI (m.p. in. °C.) |
|---|---|---|
| 55 | 31 | 1,2-dimethyl-1H—imidazo[4,5-c]quinolin-5-oxide (234–237) |
| 56 | 33 | 8-chloro-1,2-dimethyl-1H—imidazo[4,5-c]-quinolin-5-oxide (not taken) |
| 57 | 124 (Part C) | 1-benzyl-1H—imidazo[4,5-c]-quinolin-5-oxide (241–251) |
| 58 | 126 (Part C) | 1-cyclohexylmethyl-1H—imidazo[4,5-c]-quinolin-5-oxide (224–226, dec.) |
| 59 | 36 | 1-ethyl-2-methyl-1H—imidazo[4,5-c]-quinolin-5-oxide (220–222) |
| 60 | 37 | 1,8-dimethyl-1H—imidazo[4,5-c]quinolin-5-oxide (265–268) |
| 61 | 38 | 1,2,8-trimethyl-1H—imidazo[4,5-c]quinolin-5-oxide (not taken) |
| 62 | 39 | 1-ethyl-1H—imidazo[4,5-c]quinolin-5-oxide (not taken) |
| 63 | 40 | 1-isobutyl-8-methyl-1H—imidazo[4,5-c]-quinolin-5-oxide (not taken) |
| 64 | 41 | 8-fluoro-1-methyl-1H—imidazo[4,5-c]-quinolin-5-oxide (not taken) |
| 65 | 42 | 7-chloro-1-isobutyl-1H—imidazo[4,5-c]-quinolin-5-oxide (not taken) |
| 66 | 43 | 1-phenyl-1H—imidazo[4,5-c]quinolin-5-oxide (222–225) |
| 67 | 44 | 1-(4-methoxyphenyl)-1H—imidazo[4,5-c]-quinolin-5-oxide (245–247) |
| 68 | 45 | 1-(4-fluorophenyl)-2-methyl-1H—imidazo-[4,5-c]quinolin-5-oxide (245–248) |
| 69 | 46 | 1-(4-methoxyphenyl)-2-methyl-1H—imidazo-[4,5-c]quinolin-5-oxide (211–213) |
| 70 | 47 | 1-(4-fluorophenyl)-1H—imidazo[4,5-c]-quinolin-5-oxide (257–259) |
| 71 | 136 | 2-methyl-1-[2-(phenyl)ethyl]-1H—imidazo-[4,5-c]quinolin-5-oxide (204–206) |
| 72 | 130 (Part B) | 1-[2-(phenyl)ethyl]-1H—imidazo[4,5-c]-quinolin-5-oxide (73–95) |
| 73 | 50 | 1-methyl-1H—imidazo[4,5-c]quinolin-5-oxide (241–244) |
| 74 | 131 | 1-benzyl-2-methyl-1H—imidazo[4,5-c]quinolin-5-oxide (193–196) |
| 75 | 52 | 1-isobutyl-2-methyl-1H—imidazo[4,5-c]-quinolin-5-oxide (214–216) |
| 76 | 53 | 1,2-dimethyl-8-fluoro-1H—imidazo[4,5-c]-quinolin-5-oxide (not taken) |

EXAMPLE 77

Preparation of a Compound of Formula VII

A mixture of 9.95 g (0.0412 mole) of 1-isobutyl-1H-imidazo [4,5-c]quinolin-5-oxide (from Example 54) and 100 ml of phosphorus oxychloride was heated at its reflux temperature for 2.5 hours, and was then cooled and poured into ice with stirring. Basification (to pH 9–10) with 50% aqueous sodium hydroxide solution was followed by extraction with dichloromethane. The extracts were dried over sodium chloride and sodium bicarbonate, and were then evaporated to provide a solid residue. A sample of the residue was recrystallized from diethyl ether to provide 4-chloro-1-isobutyl-1H-imidazo [4,5-c]quinoline, m.p. 134°–136° C. Analysis: Calculated for $C_{14}H_{17}ClN_3$: %C, 64.7; H, 5.4; %N, 16.2; Found: %C, 64.3; %H, 5.3; %N, 16.3.

Using the method of Example 77, intermediate compounds of Formula VII shown in Table V were prepared.

TABLE V

| Ex. No. | Intermediate of Formula VI (Example No.) | Intermediate of Formula VII (m.p. in °C.) |
|---|---|---|
| 78 | 55 | 4-chloro-1,2-dimethyl-1H—imidazo[4,5-c]-quinoline (198–200) |
| 79 | 56 | 4,8-dichloro-1,2-dimethyl-1H—imidazo-[4,5-c]quinoline (not taken) |
| 80 | 57 | 1-benzyl-4-chloro-1H—imidazo[4,5-c]-quinoline (160–167) |
| 81 | 58 | 4-chloro-1-(cyclohexylmethyl)-1H—imidazo[4,5-c]quinoline (176–179) |
| 82 | 59 | 4-chloro-1-ethyl-2-methyl-1H—imidazo-[4,5-c]quinoline (170–172) |
| 83 | 60 | 4-chloro-1,8-dimethyl-1H—imidazo[4,5-c]-quinoline (233–237) |
| 84 | 61 | 4-chloro-1,2,8-trimethyl-1H—imidazo-[4,5-c]quinoline (243–247) |
| 85 | 62 | 4-chloro-1-ethyl-1H—imidazo[4,5-c]-quinoline (not taken) |
| 86 | 63 | 4-chloro-1-isobutyl-8-methyl-1H—imidazo-[4,5-c]quinoline (202–205) |
| 87 | 64 | 4-chloro-8-fluoro-1-methyl-1H—imidazo-[4,5-c]quinoline (not taken) |
| 88 | 65 | 4,7-dichloro-1-isobutyl-1H—imidazo-[4,5-c]quinoline (not taken) |
| 89 | 66 | 4-chloro-1-phenyl-1H—imidazo[4,5-c]-quinoline (not taken) |
| 90 | 67 | 4-chloro-1-(4-methoxyphenyl)-1H—imidazo[4,5-c]quinoline (210–212) |
| 91 | 68 | 4-chloro-1-(4-fluorophenyl)-2-methyl-1H—imidazo[4,5-c]quinoline (295–297) |
| 92 | 69 | 4-chloro-1-(4-methoxyphenyl)-2-methyl-1H—imidazo[4,5-c]quinoline (211–213) |
| 93 | 70 | 4-chloro-1-(4-fluorophenyl)-1H—imidazo[4,5-c]quinoline (248–250) |
| 94 | 72 | 4-chloro-1-[2-(phenyl)ethyl]-1H—imidazo[4,5-c]quinoline (176–188) |
| 95 | 73 | 4-chloro-1-methyl-1H—imidazo[4,5-c]-quinoline (179–181) |
| 96 | 74 | 1-benzyl-4-chloro-2-methyl-1H—imidazo[4,5-c]quinoline (216–218) |
| 97 | 75 | 4-chloro-1-isobutyl-2-methyl-1H—imidazo-[4,5-c]quinoline (152–155) |
| 98 | 76 | 4-chloro-1,2-dimethyl-8-fluoro-1H—imidazo[4,5-c]quinoline (not taken) | lated for $C_{12}H_{12}N_4$: % C, 67.9; % H, 5.7; % N, 26.4; Found: % C, 67.6; H, 5.4; % N, 26.3.

Using the general method exemplified in Examples 99 and 100 compounds of the invention of Formula I shown in Table VI were prepared.

TABLE VI

| Ex. No. | Intermediate Formula VII (Example No.) | Product of Formula I (m.p. in °C.) |
|---|---|---|
| 101 | 83 | 1,8-dimethyl-1H—imidazo[4,5-c]-quinolin-4-amine (305–309) |
| 102 | 121, Part D | 1-(2,3-dihydroxypropyl)-1H—imidazo[4,5-c]quinolin-4-amine (228–230) |
| 103 | 84 | 1,2,8-trimethyl-1H—imidazo[4,5-c]quinolin-4-amine (>250) |
| 104 | 86 | 1-isobutyl-8-methyl-1H—imidazo-[4,5-c]quinolin-4-amine hydrate (206–208) |
| 105 | 95 | 1-methyl-1H—imidazo[4,5-c]quinolin-4-amine (270–272) |
| 106 | 89 | 1-phenyl-1H—imidazo[4,5-c]quinolin-4-amine (278–280) |
| 107 | 90 | 1-(4-methoxyphenyl)-1H—imidazo[4,5-c]quinolin-4-amine (286–288) |
| 108 | 92 | 1-(4-methoxyphenyl)-2-methyl-1H—imidazo[4,5-c]quinolin-4-amine (263–265) |
| 109 | 91 | 1-(4-fluorophenyl)-2-methyl-1H—imidazo[4,5-c]quinolin-4-amine (296–299) |
| 110 | 93 | 1-(4-fluorophenyl)-1H—imidazo-[4,5-c]quinolin-4-amine (290–293) |
| 111 | 79 | 8-chloro-1,2-dimethyl-1H—imidazo-[4,5-c]quinolin-4-amine (283–286) |
| 112 | 88 | 7-chloro-1-isobutyl-1H—imidazo-[4,5-c]quinolin-4-amine hydrate (211–214) |
| 113 | 97 | 1-isobutyl-2-methyl-1H—imidazo-[4,5-c]quinolin-4-amine (200–202) |
| 114 | 98 | 1,2-dimethyl-8-fluoro-1H—imidazo-[4,5-c]quinolin-4-amine hydrate (262–264) |

EXAMPLE 99

Preparation of a Compound of Formula I

A mixture of 4.0 g (0.0154 mole) of 4-chloro-1-isobutyl-1H-imidazo [4,5-c]quinoline (from Example 77) and 25 cc of concentrated ammonium hydroxide was placed in a metal bomb and heated at 150° C. for about 16 hours. After cooling the solid was separated by filtration, washed with water and recrystallized from ethanol to provide white crystals of 1-isobutyl-1H-imidazo [4,5-c]quinolin-4-amine, m.p. 288°–291° C. Recrystallization from N,N-dimethylformamide is preferred. Analysis: Calculated for $C_{14}H_{16}N_4$: % C, 70.0; H, 6.7; % H, 23.3; Found: % C, 69.3; % H, 6.6; % N, 23.2.

EXAMPLE 100

Alternative Preparation of a Compound of Formula I

A mixture of 2.0 g (0.00863 mole) of 4-chloro-1,2-dimethyl-1H-[4,5-c]imidazo quinoline (from Example 78) and 30 ml of 15% ammonia in methanol was heated in a steel bomb for 18 hours at 155° C. The bomb was cooled, and the solide was separated by filtration, washed with ethanol and recrystallized from ethanol to provide white needles of 1,2-dimethyl-1H-imidazo [4,5-c]quinolin- 4-amine, m.p. 288°–290° C. Analysis: Calcu-

EXAMPLE 115

To a stirred. cold (5° C.) mixture of 29.1 g (0.136 mole) of 1-(2-hydroxyethyl)-1H-imidazo[4,5-c]quinoline (from Example 34) and 500 ml of pyridine was added, in small portions, 23.9 g (0.17 mole) of benzoyl chloride. The mixture was permitted to warm to about 20° C. The solution was evaporated, and water was added to the residue. The solid was separated by filtration, washed with water and recrystallized from a 50:50 ethyl acetate/hexane mixture. Recrystallization from ethyl acetate and again from ethanol provided white crystals of 1 (2-benzoloxyethyl)-1H-imidazo-[4,5-c]quinoline, m.p. 149°–151° C. Analysis: Calculated for $C_{19}H_{15}N_3O_2$: % C, 71.9; % H, 4.8; % N, 13.2; Found: % C, 71.8: % H, 4.6; % N, 13.2.

EXAMPLE 116

A mixture of 67.5 g (0.213 mole) of 1-(2-benzoyloxyethyl)-1H-imidazo[4,5-c]quinoline (from Example 115), 36.3 g (0.32 mole) of 30% hydrogen peroxide and 450 ml of glacial acetic acid was heated at 65° C. for 2 days with stirring. The solution was evaporated in vacuo, and the residue was then added to water. The mixture was neutralized with aqueous sodium hydroxide solution and sodium bicarbonate. The solid was separated by filtration, washed with water and recrystallized form methanol to provide tan solid 1-(2-benzoyloxyethyl)-1H-imidazo[4,5-c]-quinolin-5-oxide.

EXAMPLE 117

A mixture of 50g (0.15 mole) of 1-(2-benzoyloxyethyl)-1H-imidazo[4,5-c]quinolin-5-oxide (from Example 116) and 200 ml of phosphorus oxychloride was heated for two hours on a steam bath. The mixture was then partially evaporated in vacuo. The mixture was poured over ice, and the solution was neutralized with sodium hydroxide. The product was separated by filtration and dissolved in dichloromethane, and the solution was washed with aqueous sodium bicarbonate solution and dried. Evaporation provided a solid which was recrystallized from a 50:50 methanol:dichloromethane solution to provide white 1-(2-benzoyloxyethyl)-4-chloro-1H-imidazo[4,5-c]quinoline, m.p. 186°–190,C. Analysis: Calculated for $C_{19}H_{14}ClN_3O_2$: % C, 64.9; % H, 4.0; % N, 12.0; Found: % C, 64.8; % H, 3.8; % N, 12.1.

EXAMPLE 118

A mixture of 25.3 g (0.072 mole) of 1-(2-benzoyloxyethyl)-4-chloro-1H-imidazo[4,5-c]quinoline (from Example 117) and 500 ml of 10% ammonia in methanol was stirred at about 20° C. for three days, and was then filtered and finally evaporated to low volume. The slurry was mixed with diethyl ether, and the solid was separated by filtration, washed with ether and recrystallized from methanol to provide white crystals of 4-chloro-1-(2-hydroxyethyl)-1H-imidazo[4,5-c]quinoline, m.p. 185°–187° C. Analysis: Calculated for $C_{12}H_{10}ClN_3O$: % C, 58.2; % H, 4.1; N, 17.0; Found: % C, 58.0; % H, 4.0; % N, 17.3.

EXAMPLE 119

A mixture of 1.3 g (0.0037 mole) of 1-(2-benzoyloxyethyl)-4-chloro-1H-imidazo[4,5-c]quinoline (from Example 117) in 60 ml of methanol was saturated with about 10g of ammonia gas. The mixture was heated at 150° C. in a steel bomb for ten hours. The mixture was evaporated, and the residue was slurried in diethyl ether and filtered. The solid obtained was slurried in methanolic hydrochloric acid to provide off-white solid 1-(2-hydroxyethyl)-1H-imidazo[4,5-c]quinolin-4-amine hydrochloride hydrate, m.p. >250° C. Analysis: Calculated for $C_{12}H_{12}N_4O \cdot HCl \cdot 1.25H_2O$: C, 50.2; % H, 5.4; % N, 19.5; Found: % C, 50.2; % H, 5.2; % N, 19.1.

EXAMPLE 120

Part A

Using the method of Example 115, benzoyl chloride was reacted with 1-(2,3-dihydroxypropyl)-1H-imidazo[4,5-c]-quinoline (from Example 51) to provide 1-(2,3-dibenzoyloxypropyl)-1H-imidazo[4,5-c]quinoline.

Part B

The crude product from Part A was reacted with hydrogen peroxide according to the method of Example 116 to provide 1-(2,3-dibenzoyloxypropyl)-1H-imidazo[4,5-c]-quinolin-5-oxide as a pale yellow solid, the melting point of the crude material being 73°–82° C.

Part C

The product from Part B was reacted with phosphorus oxychloride according to the method of Example 117 to provide 4-chloro-1-(2,3-dibenzoyloxypropyl)-1H-imidazo[4,5-c]quinoline, m.p. 162°–165° C. after recrystallization from ethanol. Analysis: Calculated for $C_{27}H_{20}ClN_3O_4$: % C, 66.7; % H, 4.1; % N, 8.6; Found: % C, 66.3; H, 3.9; % N, 8.4.

Part D

Hydrolysis of the product from Part C according to the method of Example 118 to provide 4-chloro-1-(2,3-dihydroxypropyl)-1H-imidazo[4,5-c]quinoline.

EXAMPLE 121

Part A 1-(2,3-Dihydroxypropyl)-1H-imidazo[4,5-c]quinoline (from Example 51) was reacted with excess acetic anhydride to provide 1-(2,3-diacetoxypropyl-1H-imidazo[4,5-c]quinoline.

Part B

The product of Part A was reacted with hydrogen peroxide according to the method of Example 116 to provide 1-(2,3-diacetoxypropyl)-1-H-imidazo[4,5-c]quinolin-5-oxide as a brownish-yellow solid, the crude melting point of which being 84°–96° C. Recrystallization from ethanol provided solid product, m.p. 223°–225° C. Analysis: Calculated for C13H12ClN3O2 % C, 56.2, % H, 4.4; N, 15.1; Found: % C, 55.8, % H, 4.3; % N, 15.1.

EXAMPLE 122

To a stirred solution of 4.0 g (0.0117 mole) of 1-(2,3-diacetoxypropyl)-1H-imidazo[4,5-c]quinolin-5-oxide (from Example 121, Part A) in 50 ml of methanol was added about 12 drops of 25% sodium methoxide solution. After one hour the product was collected by filtration, washed with methanol and recrystallized from ethanol to provide 1-(2,3-dihydroxypropyl)-1H-imidazo[4,5-c]quinolin-5-oxide, m.p. 240°–242° C. Analysis: Calculated for $C_{13}H_{13}N_3O_3$: % C, 60.2; % H, 5.1; % N, 16.2; Found: % C, 60.0; % H, 5.0; % N, 15.8.

EXAMPLE 123

Excess acetic anhydride (100 ml) was refluxed for 0.5 hour with 1-(2,3-dihydroxypropyl)-2-methyl-1H-imidazo[4,5-c]quinoline (from Example 35) to provide 1-(2,3-diacetoxypropyl)-2-methyl-1H-imidazo[4,5-c]quinoline. This product was reacted with hydrogen peroxide using the method of Example 120 to provide 1-(2,3-diacetoxypropyl)-2-methyl-1H-imidazo[4,5-c]quinolin-5-oxide as a yellow solid. This crude product was reacted with phosphorus oxychloride according to the method of Example 121 to provide the product 4-chloro-(2,3-diacetoxypropyl)-2-methyl-1H-imidazo[4,5-c]quinoline. This product was dissolved in methanol saturated with ammonia and stirred for three days. The product obtained was 4-chloro-1-(2,3-dihydroxypropyl)-2-methyl-1H-imidazo[4,5-c]quinoline.

EXAMPLE 124

Part A

Using the method of Example 1, benzylamine and 4-chloro-3-nitroquinoline were reacted to provide 4-benzylamino-3-nitroquinoline. The structural assignment for the crude product (m.p. 178°–196° C.) was supported by infrared spectral analysis.

Part B

Using the method of Example 16, 42.2 g (0.15 mole) of 4-benzylamino-3-nitroquinoline was reduced to provide 3-amino-4-(benzylamino)quinoline as a tan solid.

Part C

To the product from Part B was added 48.7 g (0.5 mole) of diethoxymethyl acetate, and the mixture was heated on a steam bath for one hour, and was then maintained at reflux for 0.5 hour. The solution was added to a stirred excess of concentrated ammonium hydroxide. The solid was separated by filtration and washed sequentially with water, 10:1 diethyl ether:ethanol, and 1:1 hexane:diethyl ether. Recrystallization from isopropanol provided pale yellow needles of 1-benzyl-1H-imidazo[4,5-c]quinoline, m.p. 178°–181° C. Analysis: Calculated for $C_{17}H_{13}N_3$: % C, 78.7; H, 5.1; % N, 16.2; Found: % C, 78.6; % H, 4.8; % N, 16.3.

EXAMPLE 125

Using the method of Example 100, 1-benzyl-4-chloro-1H-imidazo[4,5-c]quinoline (from Example 80) was reacted with ammonia to provide white solid 1-benzyl-1H-imidazo[4,5-c]quinolin-4-amine after recrystallization from N,N-dimethylformamide, m.p. 257°–259° C. Analysis: Calculated for $C_{17}H_{14}N_4$: % C, 74.4; % H, 5.1; % N, 20.4; Found: % C, 74.3; % H, 5.4; % N, 20.5.

EXAMPLE 126

Part A

A mixture of 26.1g (0.125 mole) of 4-chloro-3-nitroquinoline, 16.4 g (0.1275 mole) of 95% cyclohexylmethylamine and 16.5 g (0.125 mole) of 95% diisopropyl ethylamine in 300 ml of tetrahydrofuran was heated on a steam bath for 0.5 hour. The solution was evaporated, and the residue was then slurried in methanol, filtered and washed with methanol. Recrystallization from methanol provided yellow platelets of 4-cyclohexylmethylamino-3-nitroquinoline, m.p. 140°–142° C. Analysis: Calculated for $C_{16}H_{19}N_3O_2$ % C, 67.3; % H, 6.7; % N, 14.7; Found: % C, 67.3; % H, 6.6; % N, 14.7.

Part B

Using the method of Example 16, 17 g (0.60 mole) of 4-cyclohexylmethylamino-3-nitroquinoline was reduced to provide 3-amino-4-(cyclohexylmethylamino)-quinoline.

Part C

The crude product from Part B was heated at reflux for 2.5 hours in 250 ml of 98% formic acid to provide 1-cyclohexylmethyl-1H-imidazo[4,5-c]quinoline as a pale yellow solid.

Example 127

Using the method of Example 100, 4-chloro-1-cyclohexylmethyl-1H-imidazo[4,5-c]quinoline (from Example 81) was aminated to provide solid 1-cyclohexylmethyl-1H-imidazo[4,5-c]quinolin-4-amine hydrate. Analysis: Calculated for $C_{17}H_{20}N_4 \cdot H_2O$: % C, 68.4; % H, 7.4; % N, 18.8; Found: % C, 68.2; H, 7.4; % N, 18.5.

EXAMPLE 128

Using the method of Example 1, 4-chloro-3-nitroquinoline was reacted with 4-chlorobenzylamine to provide yellow solid 4-(4-chlorobenzylamino)-3-nitroquinoline, the melting point of the crude product being 168°–173° C.

EXAMPLE 129

Using the method of Example 1, 4-chloro-3-nitroquinoline was reacted with 2-(phenyl)ethylamine to provide yellow solid 3-nitro-4-[2-(phenyl)ethylamino]quinoline, the melting point of the crude product being 174°–180° C.

EXAMPLE 130

Part A

Using the method of Example 16, 3-nitro-4-[2-(phenyl)ethylamino]quinoline from Example 129 was reduced to provide 3-amino-4-[2-(phenyl)ethylamino]-quinoline.

Part B

Using the method of Example 31, 3-amino-4-[2-(phenyl)ethylamino]quinoline was reacted with triethyl orthoformate and formic acid to provide 1-[2-(phenyl)ethyl]-1H-imidazo[4,5-c]quinoline, m.p. 105°–108° C.

EXAMPLE 131

Using the method of Example 31, 3-amino-4-(benzylamino)quinoline (from Example 124, Part B) was reacted with triethyl orthoacetate and acetic acid to provide 1-benzyl-2-methyl-1H-imidazo[4,5-c]quinoline hydrate, m.p. 145°–147° C. Analysis: Calculated for $C_{18}H_{15}N_3 \cdot 2.25H_2O$: % C, 68.9; % H, 6.3; % N, 13.4; Found: % C, 69.2; % H, 6.0; % N, 13.4.

EXAMPLE 132

Using the method of Example 100, 1-benzyl-4-o chloro-2-methyl-1H-imidazo[4,5-c]quinoline (from Example 96) was aminated to provide 1-benzyl-2-methyl-1H-imidazo[4,5-c]quinolin-4-amine, m.p. 279°–282° C. after recrystallization from N,N-dimethylformamide. Analysis: Calculated for $C_{14}H_{16}N_4$: % C, 75.0: % H, 5.6; % N, 19.4; Found; % C, 74.5; % H, 5.5; % N, 19.5.

EXAMPLE 133

A mixture of 4.0 g (0.016 mole) of 4-chloro-1-(2-hydroxyethyl)-1H-imidazo[4,5-c]quinoline (from Example 118) and 30 ml of 10% ammonia in methanol was heated in a steel bomb for 12 hours at 150° C. The resulting solid was separated from the cooled mixture by filtration, and was washed sequentially with water and methanol. The air-dried solid was recrystallized from N,N-dimethylformamide to provide white solid 1-(2-hydroxyethyl)-1H-imidazo[4,5-c]-quinolin-4-amine, m.p. 260°–262° C. Analysis: Calculated for $C_{12}H_{12}N_4O$: % C, 63.1; % H, 5.3; % N, 24.5; Found: % C, 63.0; % H, 5.2; % N, 24.3.

EXAMPLE 134

To a solution of 5.7 g (0.030 mole) of 4-hydroxy-3-nitroquinoline in 50 ml of N,N-dimethylformamide was added 9.3 g (0.060 mole) of phosphorous oxychloride. The solution was heated on a steam bath for 5 minutes, then poured with stirring into 200 ml of 40% aqueous methylamine. The mixture was heated on a steam bath for fifteen minutes, then diluted with 200 ml of water. The solid was separated by filtration, then dissolved in dilute hydrochloric acid. The solution was filtered and the filtrate was basified with ammonium hydroxide. The solid precipitate was separated by filtration, washed with water and dried to provide yellow solid 4-methylamino-3-nitroquinoline, m.p. 167°–171° C.

EXAMPLE 135

To a solution of 4.8 g (0.0311 mole) of phosphorus oxychloride in 20 ml of N,N-dimethylformamide was added in small portions 5.0 g (0.0207 mole) of 1-isobutyl-1H-imidazo[4,5-c]quinolin-5-oxide. The solution was stirred for 15 minutes at 20° C., then heated on a steam bath for 15 minutes. The solution was cooled to 20° C., then poured into stirred ice. The solution was basified to pH 8 with concentrated ammonium hydroxide. The yellow solid precipitate was separated by filtration, washed sequentially with water and diethyl ether, and dried to provide 4-chloro-1-isobutyl-1H-imidazo[4,5-c]quinoline hydrate, m.p. 103°–107° C. Recrystallization twice from ethyl acetate with drying provided 4-chloro-1-isobutyl-1H-imidazo[4,5-c]-quinoline, m.p. 135°–137° C. Analysis: Calculated for $C_{14}H_{14}ClN_3$: % C, 64.7; % H, 5.4; % N, 16.2; Found: % C, 64.6; H, 5.5; % N, 16.1.

EXAMPLE 136

Using the method of Example 31, 3-amino-4-[2-(phenyl)ethylamino]quinoline (from Example 130, Part A) was reacted with triethyl orthoacetate and acetic acid to provide 2-methyl-1-[2-(phenyl)ethyl]-1H-imidazo[4,5-c]-quinoline.

EXAMPLE 137

Alternative Preparation of a Compound of Formula I

A mixture of 6.0 g (0.023 mole) of 4-chloro-1-isobutyl-1H-imidazo[4,5-c]quinoline (from Example 77) and 30 ml of 20% ammonia in methanol was heated in a steel bomb for 18 hours at 150° C. The bomb was cooled, and the solid was separated by filtration, washed with methanol and recrystallized from N,N-dimethylformamide to provide 1-isobutyl-1H-imidazo[4,5-c]quinolin-4-amine, m.p. 292°–294° C. Analysis: Calculated for $C_{14}H_{16}N_4$: % C, 70.0; H, 6.7; % N, 23.3; Found: % C, 69.9; % H, 6.7; % N, 23.6.

EXAMPLE 138

Step (1)

To a solution of 22.5 g (0.0823 mole) of 4-(n-hexyl)amino-3-nitroquinoline in 300 ml of toluene was added about 1.0 g of 5% platinum on charcoal and the mixture was hydrogenated on a Paar apparatus for 1.5 hours. Filtration followed by evaporation in vacuo provided a residue of 3-amino-4-(n-hexyl)aminoquinoline as an orange solid. Thin layer chromatographic analysis of the product on silica gel, eluting with methanol, showed one spot at $R_f = 0.73$ and a trace at $Rf = 0.35$.

Step (2)

The crude reaction product obtained by the method of Step (1) above from 22.5 g of 4-(n-hexyl)amino-3-nitroquinoline was mixed with 17.1 (0.1152 mole) of triethyl orthoformate and the mixture was heated at 130° C. for 2.5 hours. Evaporation provided a residue which was analyzed by thin layer chromatography on a silica gel plate, eluting with methanol. One spot was detected at $R_f = 0.8$. A small sample of the residue was recrystallized once from diethyl ether to provide solid 1-(n-hexyl)-1H-imidazo-4,5-c]quinoline, m.p. 75°–77° C. Analysis: Calculated for $C_{16}H_{19}N_3$: % C, 75.85; % H, 7.55; % N, 16.6; Found:% C, 75.7; % H, 7.7; % N, 16.7

Step (3)

The crude reaction product from Step (2) above was diluted with 125 ml of glacial acetic acid and 14.0 g (0.1235 mole) of 30% hydrogen peroxide, and the mixture was heated at a bath temperature of 70° C. for 22 hours. The glacial acetic acid was removed by adding heptane and by then effecting an azeotropic distillation. The residue was diluted and neutralized with saturated sodium bicarbonate solution. The solid obtained was separated by filtration, washed with water, slurried in diethyl ether, separated by filtration and dried. Recrystallization from ethyl acetate provided 11.8 g of solid 1-(n-hexyl)-1H-imidazo[4,5-c]-quinolin-5-oxide, m.p. 153°–158° C.

Step (4)

To a mixture of 6.1 ml (0.0657 mole) of phosphorus oxychloride and 80 ml of N,N-dimethylformamide was added gradually, with cooling to 10°–20° C., 11.8 g (0.0438 mole) of 1-(n-hexyl)-1H-imidazo[1,5-c]quinolin-5-oxide. The solution was allowed to stand at 20° C. for 15 minutes, and was then heated on a steam bath for 30 minutes. The solution was cooled and poured over ice with stirring. To the mixture was added concentrated ammonium hydroxide to adjust the pH to 8 to 9. The solid was separated by filtration, washed sequentially with water and diethyl ether, and dried. Recrystallization of a small portion of product from 1:1 ethyl acetate;hexane provided white solid 4-chloro-1-(n-hexyl)-1H-imidazo[4,5-c]quinoline, m.p. 106°–108° C. Analysis: Calculated for $C_{16}H_{18}ClN_3$; % C 66.8; H, 6.3; % N, 14.6; Found % C, 66.8; % H, 6.1: % N, 14.4.

Step (5)

A mixture of 8.9 g (0.0308 mole) of 4-chloro-1-(n-hexyl)-1H-imidazo[4,5-c]quinoline and 75 ml of 20% ammonia in methanol was placed in a metal bomb and heated at 150° C. for about 8 hours. After cooling, the solid was separated by filtration, washed with methanol and recrystallized from ethanol. The product was white solid 1-(n-hexyl)-1H-imidazo[4,5-c]quinolin-4-amine, m.p. 189°–191° C. Analysis: Calculated for $C_{16}H_{20}N_4$ % C, 71.6; H, 7.5; % N, 20.9; Found: % C, 71.4; % H, 7.4; % N, 21.0.

Using the method of Example 1 and/or 2, and starting with the indicated substituted quinolines and primary amines, the following compounds of Formula III were prepared (Table II).

TABLE VII

| Ex. No. | Quinoline Starting Material of Formula IIB | Primary Amine Starting Material | Intermediate of Formula III (m.p. in. °C.) |
|---|---|---|---|
| 139 | 4-chloro-3-nitroquinoline | 4-chlorobenzylamine | 4-(4-chlorobenzylamino)-3-nitroquinoline (175–177) |
| 140 | 4-chloro-3-nitroquinoline | n-octylamine | 4-(n-octylamino)-3-nitroquinoline (50–52) |
| 141 | 4-chloro-3-nitroquinoline | 1-(phenyl)ethylamine | 4-[1-(phenyl)ethylaminol]-3-nitroquinoline (138–141) |
| 142 | 4-chloro-3-nitroquinoline | 1,3-dimethylbutylamine | 4-(1,3-dimethylbutylamino)-3-nitroquinoline (66–68) |

TABLE VII -continued

| Ex. No. | Quinoline Starting Material of Formula IIB | Primary Amine Starting Material | Intermediate of Formula III (m.p. in °C.) |
|---|---|---|---|
| 143 | 4-chloro-6,7-dimethoxy-3-nitroquinoline | isobutylamine | 6,7-dimethoxy-4-isobutylamino-3-nitroquinoline |

EXAMPLE 144 method of Example 138, Step (2), to provide the intermediates of Formula V shown in Table III.

TABLE VIII

| Ex. No. | Intermediate of Formula III (Example) | Intermediate of Formula IV | Ortho Ester | Intermediate of Formula V (m.p. in °C.) |
|---|---|---|---|---|
| 145 | 139 | 3-amino-4-(4-chlorobenzylamino)quinoline | triethyl orthoacetate | 1-(4-chlorobenzyl)-2-methyl-1H—imidazo[4,5-c]quinoline (178–180) |
| 146 | 138 Step (2) | 3-amino-4-(n-hexylamino)quinoline | triethyl orthoacetate | 1-(n-hexyl)-2-methyl-1H—imidazo[4,5-c]quinoline (88–90) |
| 147 | 2 | 3-amino-4-(methylamino)quinoline | triethyl orthoisobutyrate | 2-isobutyl-1-methyl-1H—imidazo[4,5-c]quinoline (125–127) |
| 148 | 140 | 3-amino-4-(n-octylamino)quinoline | triethyl orthoformate | 1-(n-octyl)-1H—imidazo[4,5-c]quinoline (not taken) |
| 149 | 1 | 3-amino-4-(isobutylamino)quinoline | triethyl orthoisobutyrate | 1,2-diisobutyl-1H—imidazo[4,5-c]quinoline (93–95) |
| 150 | 129 | 3-amino-4-[2-(phenyl)ethylamino]quinoline | triethyl orthoisobutyrate | 2-isobutyl-1-[2-(phenyl)ethyl]1H—imidazo[4,5-c]quinoline (92–94) |
| 151 | 141 | 3-amino-4-[1-(phenyl)ethylamino]quinoline | triethyl orthoformate | 1-[1-(phenyl)ethyl]-1H—imidazo[4,5-c]quinoline (172–174) |
| 152 | 142 | 3-amino-4-(1,3-dimethylbutylamino)quinoline | triethyl orthoformate | 1-(1,3-dimethylbutyl)-1H—imidazo-[4,5-c]quinoline (83–85) |
| 153 | 143 | 3-amino-6,7-dimethoxy-4-(isobutylamino)quinoline | triethyl orthoformate (a few drops of formic acid) | 7,8-dimethoxy-1-isobutyl-1H—imidazo-[4,5-c]quinoline (163–165) |

Using the method of Example 138, Step (1), 6,7-dimethoxy-4-isobutylamino-3-nitroquinoline was reduced to 3-amino-6,7-dimethoxy-4-isobutylaminoquinoline, m.p. 159°–161° C.

Using the method of Example 138, Step (1), various intermediates of Formula III were reduced to provide 3-aminoquinolines of Formula IV. These intermediates of Formula IV (usually crude) were cyclized using the Using the method of Example 138, step (3), intermediate compounds of Formula VI shown in Table IX were prepared.

TABLE IX

| Ex. No. | Intermediate of Formula V (Example No.) | Intermediate of Formula VI (m.p. in °C.) |
|---|---|---|
| 154 | 145 | 1-(4-chlorobenzyl)-2-methyl-1H—imidazo[4,5-c]quinolin-5-oxide (251–253) |
| 155 | 48 | 1-(n-butyl)-1H—imidazo[4,5-c]quinolin-5-oxide (161–163) |
| 156 | 146 | 1-(n-hexyl)-2-methyl-1H—imidazo[4,5-c]quinolin-5-oxide (138–148 crude) |
| 157 | 147 | 2-isobutyl-1-methyl-1H—imidazo[4,5-c]quinolin-5-oxide (202–204) |
| 158 | 148 | 1-(n-octyl)-1H—imidazo[4,5-c]quinolin-5-oxide (86–90) |
| 159 | 149 | 1,2-diisobutyl-1H—imidazo[4,5-c]quinolin-5-oxide (153–156) |
| 160 | 150 | 2-isobutyl-1-[2-(phenyl)ethyl]-1H—imidazo[4,5-c]quinolin-5-oxide (158–160) |
| 161 | 151 | 1-[1-(phenyl)ethyl]-1H—4,5-c]quinolin-5-oxide (not taken), yellow solid, satisfactory elemental analysis |
| 162 | 152 | 1-(1,3-dimethylbutyl)-1H—imidazo[4,5-c]quinolin-5-oxide (not taken), light orange solid |
| 163 | 153 | 7,8-dimethoxy-1-isobutyl-1H—imidazo[4,5-c]quinolin-5-oxide (not taken) |

Using the method of Example 138, Step (4), intermediate compounds of Formula VII shown in Table X were prepared.

TABLE X

| Ex. No. | Intermediate of Formula VI (Example No.) | Intermediate of Formula VII (m.p. in °C.) |
|---|---|---|
| 164 | 71 | 4-chloro-2-methyl-1-[2-(phenyl)ethyl]-1H—imidazo[4,5-c]quinoline (138–140) |
| 165 | 154 | 1-(4-chlorobenzyl)-4-chloro-2-methyl-1H—imidazo[4,5-c]quinoline (240–242) |
| 166 | 155 | 1-(n-butyl)-4-chloro-1H—imidazo[4,5-c]quinoline (122–124) |
| 167 | 156 | 4-chloro-1-(n-hexyl)-2-methyl-1H—imidazo[4,5-c]quinoline (119–121) |
| 168 | 157 | 4-chloro-2-isobutyl-1-methyl-1H—imidazo[4,5-c]quinoline (158–160) |
| 169 | 158 | 4-chloro-1-(n-octyl)-1H—imidazo[4,5-c]quinoline (86–90) |
| 170 | 159 | 4-chloro-1,2-diisobutyl-1H—imidazo[4,5-c]quinoline (137–139) |
| 171 | 160 | 4-chloro-2-isobutyl-1-[2-(phenyl)ethyl]-1H—imidazo[4,5-c]quinoline (151–153) |
| 172 | 161 | 4-chloro-1-[1-(phenyl)ethyl]-1H—imidazo[4,5-c]quinoline (not taken), white solid, satisfactory elemental analysis |
| 173 | 162 | 4-chloro-1-(1,3-dimethylbutyl)-1H—imidazo[4,5-c]quinoline (111–114) |
| 174 | 163 | 4-chloro-7,8-dimethoxy-1-isobutyl-1H—imidazo[4,5-c]quinoline (185–188) |

Using the general method exemplified in Example 138, Step (5), compounds of the invention of Formula I shown in Table XI were prepared.

residue. The solution was filtered, and the filtrate was brought to pH 8–9 with concentrated ammonium hydroxide. The resulting yellow solid was filtered, washed

TABLE XI

| Ex. No. | Intermediate of Formula VII (Example No.) | Product of Formula I (m.p. in °C.) |
|---|---|---|
| 175 | 82 | 1-ethyl-2-methyl-1H—imidazo[4,5-c]quinolin-4-amine (274–276) |
| 176 | 164 | 2-methyl-1-[2-(phenyl)ethyl]-1H—imidazo[4,5-c]quinolin-4-amine (188–190) |
| 177 | 165 | 1-(4-chlorobenzyl)-2-methyl-1H—imidazo[4,5-c]quinolin-4-amine (>300) |
| 178 | 166 | 1-(n-butyl)-1H—imidazo[4,5-c]quinolin-4-amine (274–276) |
| 179 | 94 | 1-[2-(phenyl)ethyl]-1H—imidazo[4,5-c]quinolin-4-amine (199–201) |
| 180 | 167 | 1-(n-hexyl)-2-methyl-1H—imidazo[4,5-c]quinolin-4-amine (189–191) |
| 181 | 168 | 2-isobutyl-1-methyl-1H—imidazo[4,5-c]quinolin-4-amine (222–224) |
| 182 | 169 | 1-(n-octyl)-1H—imidazo[4,5-c]quinolin-4-amine (127–129) |
| 183 | 170 | 1,2-diisobutyl-1H—imidazo[4,5-c]quinolin-4-amine (191–193) |
| 184 | 171 | 2-isobutyl-1-[2-(phenyl)ethyl]-1H—imidazo[4,5-c]quinolin-4-amine hydrate (232–235) |
| 185 | 172 | 1-[1-(phenyl)ethyl]-1H—imidazo[4,5-c]quinolin-4-amine (217–221) |
| 186 | 173 | 1-(1,3-dimethylbutyl)-1H—imidazo[4,5-c]quinolin-4-amine (158–161) |

EXAMPLE 187

To a solution of 3.5 g (0.0116 mole) of 2-methyl-1-[2-(phenyl)ethyl]-1H-imidazo[4,5-c]quinolin-4-amine in 30 ml of ethanol was added 1.2 g (0.0127 mole) of methanesulfonic acid. The mixture was heated on a steam bath for 30 minutes, the ethanol was removed by evaporation in vacuo and the residue was recrystallized from ethanol. The product was white solid 2-methyl-1-[2-(phenyl)ethyl]-H-imidazo[4,5-c]quinolin-4-amine methanesulfonate, m.p. 287°–289° C. Analysis: Calculated for $C_{19}H_{18}N_4 \cdot CH_3S_3O_3H$: % C, 0.3; % H, 5.6; % N, 14.1; Found: % C, 60.1; % H, 5.3; % N, 14.0.

Additional salts of the invention prepared by reaction of the amine with acids in ethanol as described above were:

1-isobutyl-1H-imidazo[4,5-c]quinolin-4-amine hydrochloride, m.p. >300° C.

1-isobutyl-1H-imidazo[4,5-c]quinolin-4-amine nitrate salt, m.p. 260°–262° C. (dec.)

1-isobutyl-1H-imidazo[4,5-c]quinolin-4-amine methanesulfonate hydrate, m.p. 203°–205° C.

1-n-hexyl-1H-imidazo[4,5-c]quinolin-4-amine hydrochloride, m.p. 288°–291° C.

1,2-diisobutyl-1H-imidazo[4,5-c]quinoline-4-amine hydrochloride hydrate.

EXAMPLE 188

Step (A)

To 50.0 g (0.269 mole) of 4-hydroxy-3-nitroquinoline in 300 ml of N,N-dimethylformamide in a 500 ml erlenmeyer flask was added, gradually, 44.3 g (0.2892 mole) of phosphorus oxychloride. The resulting mixture was heated on a steam bath for about 15 minutes, and was then poured onto ice with stirring. After neutralization with saturated sodium bicarbonate solution, the resulting light-colored solid was separated by filtration and washed sequentially with a saturated sodium bicarbonate solution and water. The solid was dissolved in methylene chloride and the solution obtained was dried over sodium chloride, filtered and transferred to a 2 l erlenmeyer flask. Triethylamine (159.6 g, 1.577 moles) was added at one time, followed by the slow addition of 21.2 g (0.2892 mole) of isobutylamine. After the isobutylamine had been added, the mixture was heated on a steam bath for about 30 minutes. The methylene chloride was removed by rotary evaporation. Water was added to the residue obtained, and concentrated hydrochloric acid was subsequently added to dissolve the residue. The solution was filtered, and the filtrate was brought to pH 8–9 with concentrated ammonium hydroxide. The resulting yellow solid was filtered, washed with water, and dried to provide 73.4 g of crude 4-isobutylamino-3-nitroquinoline, m.p. 114°–118° C. The product was further purified by recrystallization from ethanol.

Step (B)

4-Isobutylamino-3-nitroquinoline (31.5 g, 0.1284 moles) from Step (A) above, was dissolved in 300 ml of toluene, and about one g of platinum on charcoal was added thereto. The resulting mixture was hydrogenated on a Parr apparatus for one and one-half hours. The mixture was then heated and filtered. Toluene was removed from the filtrate by rotary evaporation to provide 27.8 g of crude 3-amino-4-(isobutylamino)quinoline. Recrystallization twice from ethyl acetate/hexane provided 18.8 g of purified product, m.p. 98°–100° C. Analysis: Calculated for $C_{13}H_{17}N_3$: % C, 72.5; % H, 8.0; % N, 19.5; Found: % C, 73.2; % H, 7.8; % N, 19.7.

Step (C)

To 10.0 g (0.0464 mole) of 3-amino-4-(isobutylamino)quinoline (from Step (B) above) was added 9.0 g (0.0604 mole) of triethyl orthoformate, and the mixture was heated at 125°–130° C. for three hours. The mixture was then allowed to cool to room temperature, and 30 ml of glacial acetic acid and 7.9 g (0.0696 mole) of 30% hydrogen peroxide solution were added thereto. The resulting mixture was heated at 68°–70° C. in an oil bath for about 24 hours. The glacial acetic acid was removed by azetropic distillation using heptane as the entrainer. Saturated sodium bicarbonate solution was added to the residue to bring it to neutrality. The beige solid which precipitated was filtered, washed with water, and dried to provide 10.0 g of crude product 1-isobutyl-1H-imidazo[4,5-c]quinolin-5-oxide. This solid was slurried in a small amount of cold acetone, and was then separated by filtration, washed and dried to provide 6.2 g of purified product having a m.p. of 205°–209° C.

Step (D)

To 40 ml of cold N,N-dimethylformamide (10°–20° C.) was added slowly 5.9 g (0.0385 mole) of phosphorus oxychloride with swirling, the temperature of the mixture being maintained at 10–20° C. 1-Isobutyl-1H-imidazo[4,5-c]quinolin-5-oxide (6.2 g; 0.0257 mole) from Step (C) above was added gradually with swirling and cooling. After addition was complete, the solution was allowed to stand at room temperature for about 30 minutes with occasional swirling. The solution was then heated on a steam bath for thirty minutes. After allowing it to cool, the solution was poured onto ice with stirring, and the resulting mixture was brought to pH 8-9 with concentrated ammonium hydroxide. The resulting off-white solid was filtered, washed with water, rinsed with ether, and dried to provide 6.0 g of crude 4-chloro-1-isobutyl-1H-imidazo[4,5-c]quinoline having a m.p. of 135°–138° C.

Step (E)

A mixture of 6.0 g (0.0231 mole) of 4-chloro-1-isobutyl-1H-imidazo[4,5-c]quinoline from Step (D) above and 30 ml of 20% ammonia in methanol was heated in a steel bomb for about 8 hours at about 145° C. The bomb was allowed to stand overnight at room temperature. The bomb was then cooled in an ice bath, and the solid therein was filtered, washed with methanol, and dried. Recrystallization from N,N-dimethylformamide provided 4.1 g of 1-isobutyl-1H-imidazo[4,5-c]quinolin-4-amine, m.p. 288°–291° C.

EXAMPLE 189

Step A

Using the method of Example 1, 4-chloro-3-nitroquinoline was reacted with 2-hydroxy-2-methylpropylamine to provide 4-(2-hydroxy-2-methylpropylamino)3-nitroquinoline, m.p. 234°–244° C. (dec.).

Analysis: Calculated for $C_{13}H_{15}N_3O_3$: % C, 59.8; % H, 5.8; % N, 16.0; Found: % C, 59.8 % H, 5.9; % N 16.1.

Part B

Using the method of Example 16, 7.0 g (0.027 mole) of 4-(2-hydroxy-2-methylpropylamino)-3-nitroquinoline, 1 g of platinum on charcoal, 200 ml of toluene and 150 ml of ethanol was hydrogenated on a Paar apparatus. The solution was filtered, then evaporated to dryness to provide 3-amino-4-(2-hydroxy-2-methylpropylamino)quinoline as a solid residue. To the residue was added 50 ml of triethyl orthoformate and 5 drops of formic acid. The solution was heated at 135° to 140° C. for one hour, then allowed to stand for about 16 hours. The product was separated by filtration, dissolved in hydrochloric acid and reprecipitated with sodium hydroxide solution. The product was recrystallized from ethanol to provide 1-(2-hydroxy-2-methylpropyl)-1H-imidazo[4,5-c]quinoline hydrate, m.p. 169°–170° C. Analysis: Calculated for $C_{14}H_{15}N_3O \cdot H_2O$: % C, 64.8; % H, 6.6; % N, 16.2; Found: % C, 65.1: % H, 6.6; % N, 16.4.

Part C

A solution of 4.0 g (0.017 mole) of 1-(2-hydroxy-2-methylpropyl)-1H-imidazo[4,5-c]quinoline in 3.8 ml of acetic anhydride and 50 ml of pyridine was heated on a steam bath for one hour, diluted with 25 ml of methanol and heated again on the steam bath for fifteen minutes. The solution was evaporated to dryness, then co-evaporated with heptane. The solid residue was dried, then a mixture of 3.6 ml of 30 percent aqueous hydrogen peroxide and 50 ml of of acetic acid was added. The mixture was heated at 60° C. for four hours, then one ml of hydrogen peroxide was added and the solution was maintained at 60° to 65° C. for 16 hours. Evaporation of the solution provided a solid residue. Infrared spectral analysis of the crude solid showed partial acetylation to the desired product, 1-(2-acetoxy-2-methylpropyl)-1H-imidazo[4,5-c]quinolin-5-oxide.

Part D

To a stirred solution of 1.5 g of crude product from Step (C) in 10 ml of dichloromethane and 2 ml of N,N-dimethylformamide was added 0.843 g (0.0055 mole) of phosphorus oxychloride. After stirring for one hour the mixture was evaporated to dryness. Hydrochloric acid was added to the residue, then the mixture was basified with ammonium hydroxide. The product was separated by filtration, washed with water and dried. Recrystallization from ethanol of a portion of the product provided 4-chloro-1-(2-hydroxy-2-methylpropyl)-1H-imidazo[4,5-c]-quinoline, m.p. 196°–199° C. Analysis: Calculated for $C_{14}H_{14}ClN_3O$: % C, 61.0; % H, 5.2; % N, 15.2; Found: % C, 60.9; % H, 5.3; % N, 15.1.

Part E

A mixture of 1.1 g (0.004 mole) of 4-chloro-1-(2-hydroxy-2-methylpropyl)-1H-imidazo[4,5-c]quinoline and 30 ml of 15 to 20% ammonia in methanol was heated at 150° to 160° C. for five hours in a bomb reactor. The mixture was filtered and the solid washed sequentially with methanol, ethyl acetate, water, and methanol then dried. Recrystallization from a mixture of ethyl acetate and methanol gave white solid 4-amino-1-(2-hydroxy-2-methylpropyl)-1H-imidazo[4,5-c]quinoline, m.p. 270°–272° C., Analysis: Calculated for $C_{14}H_{16}N_4O$: % C, 65.6; % H, 6.3; % N, 21.9; Found: % C, 65.6; %H, 6.3; % N, 21.9.

Alternative Reaction Replacing Step (C) Above

A mixture of 2.4 g (0.01 mole) of 1-(2-hydroxy-2-methylpropyl)-1H-imidazo[4,5-c]quinoline, 2.5 ml of acetic acid and 1.7 g of 30% aqueous hydrogen peroxide (0.015 mole) were heated at 65°–70° C. for six and one-half hours. The solvent was evaporated under a stream of nitrogen. The resulting residue was co-evaporated with heptane in vacuo. The residue was then added to water and made basic by adding ammonium hydroxide. The solid was filtered, washed with water and dried to give 2.0 g of product which by thin layer chromatrography was found to contain 1 major component, 1-(2-hydroxy-2-methylpropyl)-1H-imidazo[4,5-c]quinolin-5-oxide, which was chlorinated directly using a procedure similar to Part (D).

Compounds of Formula I indicated in Table XII below were prepared via the various intermediates indicated in Table XII. More specifically, compounds of Formula IV were reacted with the indicated trialkyl ortho ester using methods similar Example 31. The compounds of Formula V thereby obtained were then reacted using methods similar to Example 54 to provide a 5-N-oxide of Formula VI. The compounds of Formula vI were then reacted using methods similar to Example 77 to provide 5-chloro-substituted compounds of Formula VII. Finally, the compounds of Formula VII were reacted using methods similar to Example 99 to provide compounds of Formula I:

TABLE XII

| Compound of | Compound of |
|---|---|

TABLE XII-continued

| Example | Formula IV | Trialkyl ortho ester | Formula V (m.p. in °C.) |
|---|---|---|---|
| 190 | Example 16 | 3,4-(CH₃O)₂C₆H₃CH₂C(OC₂H₅)₃ | 2-(3,4-dimethoxybenzyl)-1-iBu imidazo[4,5-c]quinoline (114–117°) |
| 191 | Example 16 | C₆H₅CH₂CH₂C(OC₂H₅)₃ | 2-(2-phenylethyl)-1-iBu imidazo[4,5-c]quinoline (126–128°) |
| 192 | Example 16 | CH₃(CH₂)₆C(OC₂H₅)₃ | 2-C₇H₁₅-1-iBu imidazo[4,5-c]quinoline (58–61°) |
| 193 | Example 16 | C₆H₅CH₂C(OC₂H₅)₃ | 2-benzyl-1-iBu imidazo[4,5-c]quinoline (127–129°) |
| 194 | Example 129 | i-Bu—C(OC₂H₅)₃ | 2-i-Bu-1-(2-phenylethyl) imidazo[4,5-c]quinoline (92–94°) |

| Example | Compound of Formula VI (m.p. °C.) | Compound of Formula VII (m.p. in °C.) |
|---|---|---|
| 190 | N-oxide, 2-(3,4-dimethoxybenzyl)-1-iBu (127–129°) | 4-Cl, 2-(3,4-dimethoxybenzyl)-1-iBu (139–141°) |
| 191 | N-oxide, 2-(2-phenylethyl)-1-iBu (155–158°) | 4-Cl, 2-(2-phenylethyl)-1-iBu (159–161°) |
| 192 | N-oxide, 2-C₇H₁₅-1-iBu (121–123°) | 4-Cl, 2-C₇H₁₅-1-iBu (83–85°) |

TABLE XII-continued

| Example | Compound of Formula I (m.p. in °C.) |
|---|---|
| 193 | [imidazo[4,5-c]quinoline N-oxide, 2-CH2-phenyl, 1-iBu] (196–198°) |
| | [4-Cl imidazo[4,5-c]quinoline, 2-CH2-phenyl, 1-iBu] (135–137°) |
| 194 | [imidazo[4,5-c]quinoline N-oxide, 2-i-Bu, 1-CH2CH2-phenyl] (158–160°) |
| | [4-Cl imidazo[4,5-c]quinoline, 2-i-Bu, 1-CH2CH2-phenyl] (151–153°) |
| 190 | [4-NH2 imidazo[4,5-c]quinoline, 2-CH2-(3,4-dimethoxyphenyl), 1-iBu] (189–192°) |
| 191 | [4-NH2 imidazo[4,5-c]quinoline, 2-(CH2)2-phenyl, 1-iBu] (137–139°) |
| 192 | [4-NH2 imidazo[4,5-c]quinoline, 2-C7H15, 1-iBu] (142–144°) |
| 193 | [4-NH2 imidazo[4,5-c]quinoline, 2-CH2-phenyl, 1-iBu] (205–207°) |
| 194 | [4-NH2 imidazo[4,5-c]quinoline, 2-i-Bu, 1-CH2CH2-phenyl] (232–235°) |

EXAMPLE 195

Step A

To a solution of 24.5 g (0.1 mole) of 4-(isobutylamino)-3-nitroquinoline in 500 ml of toluene was added about 1 g of platinum on charcoal, and the mixture was hydrogenated on a Paar apparatus. The catalyst was then removed by filtration.

Step B

To the solution from Step A was added 10.6 g (0.1 mole) of benzaldehyde, and the solution was refluxed under a Dean StCark trap until no more water came over. The product was 28.3 g of a bright yellow oil after evaporation of the solvent. Thin layer chromatography revealed two spots and therefore the oil was chromatographed using a flash column and ethyl acetate as the eluent to provide 14 g of a yellow solid which appeared homogeneous by thin layer chromatography, but smelled of benzaldehyde. The solid was dissolved in toluene and 5 g of palladium on charcoal was added. After refluxing overnight, the catalyst was filtered, the toluene was evaporated and the solid was recrystallized from ethyl acetate to provide colorless crystals of 1-isobutyl-2-phenyl-1H-imidazo[4,5-c]quinoline, melting point 139°–140° C. Analysis: Calculated for $C_{20}H_{19}N$: % C, 79.7; % H, 6.4; % N, 13.9; Found: % C, 79.7, % H, 6.2; % N, 13.9.

Step C

To a solution of 7.0 g (0.0232 mole) of 1-isobutyl-2-phenyl-1H-imidazo[4,5-c]quinoline in 50 ml of acetic acid was added 3.9 g (0.035 mole) of hydrogen peroxide in the form of a 30% aqueous solution. The mixture was heated at 70° C. for one day, and was then evaporated, added to water and made basic with ammonia and filtered. The product was 6.8 g of 1-isobutyl-2-phenyl-1H-imidazo[4,5-c]quinolin-5-oxide.

Step D

Three ml (0.0321 mole) of phosphorus oxychloride and 35 ml of N,N-dimethyl formamide were mixed and 6.8 g (0.0214 mole) of 1-isobutyl-2-phenyl-1H-imidazo[4,5-c]quinolin-5-oxide was added thereto. The solution was heated on a steam batch for 30 minutes, and was then cooled and poured into ice with stirring. Basification (to pH 9–10) with ammonium hydroxide was followed by extraction with dichloromethane. The extracts were dried with magnesium sulfate, and were then evaporated to provide an oil which was slurried in hexane. The material solidified and was washed with hexane and dried to yield 6.8 g of a solid which was mainly 4-chloro-1-isobutyl-2-phenyl-1H-imidazo[4,5-c]quinoline as shown by thin layer chromatography.

Step E

A mixture of 5.6 g (0.016 mole) of 4-chloro-1-isobutyl-2-phenyl-1H-imidazo[4,5-c]quinoline and 30 ml of a 20% mixture of ammonia in methanol was placed in a metal bomb and heated at 145°–150° C. for about 6 hours. After cooling, the solid was separated by filtration, washed with methanol and dried to provide 3.8 g of crude product. Recrystallization of the solid from ethanol provided 2.4 g of colorless 1-isobutyl-2-phenyl-1H-imidazo[4,5-c]quinolin-4-amine hydrate, melting point 194°–205° C. Analysis: Calculated for $C_{20}H_{20}N_4 \cdot \frac{1}{2}H_2O$: % C, 73.8; % H, 6.5: % N, 17.2. Found: % C, 73.6; % H, 6.2: % N, 17.0

EXAMPLE 196

Step A

Following the general method of Example 195, Step A, 4-(methylamino)-3-nitroquinoline was reduced to provide 3-amino-4-(methylamino)quinoline.

Step B

Following the general method of Example 195, Step B, 3-amino-4-(methylamino)quinoline was reacted with benzaldehyde to provide 1-methyl-2-phenyl-1H-imidazo[4,5-c]quinoline, melting point 168–170° C. Analysis: Calculated for $C_{17}H_{13}N_3$: % C, 78.7; % H, 5.1; % N, 16.2. Found: % C, 78.9; % H, 5.0; % N, 16.1.

Step C

Following the general method of Example 195, Step C, 1-methyl-2-phenyl-1H-imidazo[4,5-c]quinoline was converted to 1-methyl-2-phenyl-1H-imidazo[4,5-c]quinolin-5-oxide.

Step D

Following the general method of Example 195, Step D, 1-methyl-2-phenyl-1H-imidazo[4,5-c]quinolin-5-oxide was converted to 4-chloro-1-methyl-2-phenyl-1H-imidazo[4,5-c]quinoline, melting point 205°–208° C. Analysis: Calculated for $C_{17}H_{12}ClN_3$: % C, 69.5; % H, 4.1; % N, 14.3. Found: % C, 69.0; % H, 4.0; % N, 13.9.

Step E

Following the general method of Example 195, Step E, 4-chloro-1-methyl-2-phenyl-1H-imidazo[4,5-c]quinoline was converted to 1-methyl-2-phenyl-1H-imidazo[4,5-c]quinolin-4-amine, melting point 275°–280° C. Analysis: Calculated for $C_{17}H_{14}N_4$: % C, 74.4; % H, 5.1; % N, 20.4. Found: % C, 74.1; % H, 4.8; % N, 20.7.

EXAMPLE 197

Step A

Following the general method of Example 195, Step B, 3-amino-4-(isobutylamino)quinoline was reacted with veratraldehyde to provide 2-(3,4-dimethoxyphenyl)-1-isobutyl-1H-imidazo[4,5-c]quinoline, melting point 192°–199° C. Analysis: Calculated for $C_{20}H_{23}N_3O_2$: % C, 73.1; % H, 6.4; % N, 11.6. Found: % C, 72.7; % H, 6.3; % N, 11.4.

Step B

Following the general method of Example 195, Step C, 2-(3,4-dimethoxyphenyl)-1-isobutyl-1H-imidazo[4,5-c]quinoline was converted to 2-(3,4-dimethoxyphenyl)-1-isobutyl-1H-imidazo[4,5-c]quinolin-5-oxide.

Step C

Following the general method of Example 195, Step D, 2-(3,4-dimethoxyphenyl)-1-isobutyl-1H-imidazo[4,5-c]quinoline was converted to 4-chloro-2-(3,4-dimethoxyphenyl)-1-isobutyl-1H-imidazo[4,5-c]quinoline.

Step D

Following the general method of Example 195, Step E, 4-chloro-2-(3,4-dimethoxyphenyl)-1-isobutyl-1H-imidazo[4,5-c]quinoline was converted to 2-(3,4-dimethoxyphenyl)-1-isobutyl-1H-imidazo[4,5-c]quinolin-4- amine, melting point 171°–174° C. Analysis: Calculated for $C_{20}H_{24}N_4O_2$: % C, 70.2: % H, 6.4; % N, 14.9. Found: % C, 70.0; % H, 6.4; % N, 14.8.

EXAMPLE 198

The following compounds of Formula I (Table XIII below) were suspended in 5% aqueous "Tween 80" and administred once intravaginally to one guinea pig each at a dose of about 5 mg/kg. The guinea pigs were bled 17 hours after drug treatment and the serum of each animal was separately assayed for interferon activity as follows:

The serum from above was diluted and incubated with guinea pig fibroblast cells at 37° C. overnight in 96 well microtiter plates. The incubated cells were then challenged with an inoculum of mengovirus that was sufficient to kill untreated cells in two days. Two days after such challenge, the cells were examined both microscopically and after staining with crystal violet to determine whether the cells remained intact. Table XIII contains the results of the study with activity/ml indicating the highest dilution of serum that protected cells from virus challenge. Untreated guinea pigs provided controls. A guinea pig control typically exhibits an activity/ml of less than about 100, though the activity/ml has been observed to exceed 100 and specifically has been observed to be 320, 640 and 1000.

TABLE XIII

| Compounds of Formula I | Interferon level (activity/ml) |
| --- | --- |
| 1-isobutyl-1H—imidazo[4,5-c]quinolin-4-amine | 31,250 |
| 4-amino-1-(2-hydroxy-2-methylpropyl)-1H—imidazo[4,5-c]quinoline | 400 |
| 1-(2-hydroxyethyl)-1H—imidazo[4,5-c]quinolin-4-amine | 800 |
| 1-(2,3-dihydroxypropyl)-1H—imidazo[4,5-c]-quinolin-4-amine | 800 |
| 1,8-dixethyl-1H—imidazo[4,5-c]quinolin 1-amine | 800 |
| 1-(2-(phenyl)ethyl)-1H—imidazo[4,5-c]quinolin-4-amine | 1,600 |
| 1-n-hexyl-1H—imidazo[4,5-c]quinolin-4-amine | 25,600 |
| 1-n-hexyl-2-methyl-1H—imidazo[4,5-c]quinolin-4-amine | 1,600 |
| 1-n-octyl-1H—imidazo[4,5-c]quinolin-4-amine | 12,800 |
| 1-isobutyl-2-(2-(phenyl)ethyl)-1H—imidazo[4,5-c]-quinolin-4-amine | 12,800 |

This data shows that interferon is induced in the guinea pig in response to treatment with any one of a number of compounds of the invention.

EXAMPLE 199

Interferon induction by 1-isobutyl-1H-imidazo[4,5-c]quinolin-4-amine was determined as follows:

Three monkeys were each administered 1-isobutyl-1H-imidazo[4,5-c]quinolin-4-amine hydrochloride intravenously at a single dose of 0.5 mg/kg. Each monkey in a second group of three monkeys was administered 1-isobutyl-1H-imidazo[4,5-c]quinolin-4-amine intravaginally at a single dose of 5 mg/kg using the micronized drug formulation described herein. Blood was drawn from all six monkeys immediately before drug treatment (as a control) and at 2, 4, 6 and 24 hours after drug treatment, and serum was prepared from these blood samples. Blood was also drawn at 30 hours from the monkeys that were dosed intravaginally.

Serum from the above samples was assayed for interferon as follows: Serum dilutions and human fibroblast cells, MRC-5, were incubated at 37° C. overnight in 96 well microliter plates. The incubated cells were then challenged with an inoculum of Mengovirus that was sufficiCent to kill untreated cells in two days. Two days after such challenge, the cells were examined both microscopically and after staining with crystal violet to determine whether the cells remained intact. Table XIV contains the results of the study with activity/ml indicating the highest dilution of serum that protected cells from virus challenge.

TABLE XIV

| Monkey Interferon Levels (Activity/ml) | | | | | |
| --- | --- | --- | --- | --- | --- |
| Intraveneous at 0.5 mg/kg (Serum) Hours After Treatment | | | | | |
| Monkey | Control | 2 | 4 | 6 | 24 |
| E 220 | <100 | <100 | <100 | 200 | 400 |
| E 623 | 3200 | 3200 | 6400 | 6400 | 25,600 |
| E 847 | <100 | 100 | 100 | 200 | 200 |
| Intravaginal at 5 mg/kg (Serum) Hours After Treatment | | | | | |
| Monkey | Control | 4 | 6 | 24 | 30 | 48 |
| E 855 | 1600 | 1600 | 3200 | 3200 | 1600 | 1600 |
| E 218 | 200 | 800 | 800 | 6400 | 1600 | 200 |
| E 864 | 1600 | 1600 | 1600 | 3200 | 1600 | 1600 |

These data show that 1-isobutyl-1H-imidazo[4,5-c]quinolin-4-amine induces interferon in the monkey, when administered intravaginally, as evidenced by the resulting protection of cells from challenge by Mengovirus.

What is claimed is:

1. A compound of the formula

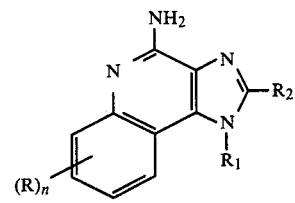

wherein $R_1$ is selected from the group consisting of alkyl of one to about ten carbon atoms, hydroxylalkyl of one to about six carbon atoms, acyloxyalkyl wherein the acyloxy moiety is alkanoyloxy of two to about four carbon atoms or benzoyloxy, and the alkyl moiety contains one to about six carbon atoms, benzyl, (phenyl)ethyl and phenyl, said benzyl, (phenyl)ethyl or phenyl substituent being optionally substituted on the benzene ring by one or two moieties independently selected from the group consisting of alkyl of one to about four carbon atoms, alkoxy of one to about four carbon atoms and halogen, with the proviso that if said benzene ring is substituted by two of said moieties, then said moieties together contain no more than 6 carbon atoms; $R_2$ is selected from the group consisting of hydrogen, alkyl of one to about eight carbon atoms, benzyl, (phenyl)ethyl and phenyl, the benzyl, (phenyl)ethyl or phenyl substituent being optionally substituted on the benzene ring by one or two moieties independently selected from the group consisting of alkyl of one to about four carbon atoms, alkoxy of one to about four carbon atoms and halogen, with the proviso that when the benzene ring is substituted by two of said moieties, then the moieties together contain no more than 6 carbon atoms; and each R is independently selected from the group consisting of alkoxy of one to about four carbon atoms, halogen and alkyl of one to about four carbon atoms, and n is an integer from 1 to 2, with the proviso that if n is 2, then said R groups together contain no more than 6 carbon atoms; or a pharmaceutically acceptable acid addition salt thereof.

2. A compound according to claim 1 wherein $R_2$ is hydrogen.

3. A compound according to claim 2 wherein R is hydrogen.

4. A compound according to claim 1, wherein $R_1$ is alkyl, benzyl, cyclohexylmethyl or hydroxyalkyl.

5. A compound according to claim 1, wherein $R_1$ is alkyl of one to about eight carbon atoms.

6. A compound according to claim 1, wherein $R_1$ is alkyl of about four to about six carbon atoms.

7. The compound 1-methyl-1H-imidazo[4,5-c]quinolin-4-amine according to claim 1.

8. The compound 1,2,8-trimethyl-1H-imidazo[4,5-c]quinolin-4-amine according to claim 1.

9. The compound 1-(2-hydroxyethyl)-1H-imidazo[4,5-c]quinolin-4-amine according to claim 1.

10. The compound 1,2-dimethyl-1H-imidazo[4,5-c]quinolin-4-amine according to claim 1.

11. The compound 1,8-dimethyl-1H-imidazo[4,5-c]quinolin-4-amine according to claim 1.

12. The compound 1-isobutyl-1H-imidazo[4,5-c]quinolin-4-amine according to claim 1.

13. The compound 1-(2,3-dihydroxypropyl)-1H-imidazo[4,5-c]quinolin-4-amine according to claim 1.

14. The compound 1-cyclohexylmethyl-1H-imidazo[4,5-c]quinolin-4-amine according to claim 1.

15. The compound 1-benzyl-1H-imidazo[4,5-c]quinolin-4-amine according to claim 1.

16. The compound 1-benzyl-2-methyl-1H-imidazo[4,5-c]quinolin-4-amine according to claim 1.

17. The compound 1-n-hexyl-1H-imidazo[4,5-c]quinolin-4-amine according to claim 1.

18. The compound 1-n-hexyl-2-methyl-1H-imidazo[4,5-c]quinolin-4-amine according to claim 1.

19. An antiviral pharmaceutical composition comprising a compound according to claim 1 and a pharmaceutically acceptable carrier, said compound being present in an amount sufficient to exert antiviral activity.

20. A method for treating a mammal infected with a virus comprising administering a compound according to claim 1 to said mammal in an amount effective to reduce severity of or prevent the infection.

21. A method treating a mammal infected with Type I or Type II Herpes simplex virus comprising administering a compound according to claim 1 to said mammal in an amount sufficient to inhibit development of lesions caused by said virus.

22. A method according to claim 21, wherein said compound is administered topically to a lesion caused by said virus.

* * * * *

UNITED STATES PATENT AND TRADEMARK OFFICE
CERTIFICATE OF CORRECTION

PATENT NO. : 4,689,338

DATED : August 25, 1987

INVENTOR(S) : John F. Gerster

It is certified that error appears in the above-identified patent and that said Letters Patent is hereby corrected as shown below:

Col. 9, line 68, "Provided" should be --provided--

Col. 11, line 64, "resulitng" should be --resulting--

Col. 12, line 3, "69.7; %7; %H, 6.3; %N, 17.4; Found %C, 69,7;" should be --69.7; %H, 6.3; %N, 17.4; Found %C, 69.7;--

Col. 12, line 67, "%C, 64.7; H, 5.4; %N," should be --%C, 64.7; %H, 5.4; %N,--

Col. 13, line 56, "%C, 70.0; H, 6.7;" should be --%C, 70.0; %H, 6.7;--

Col. 13, line 62, "dimethyl-1H-[4,5-c]imidazo quinoline" should be --dimethyl-1H-imidazo[4,5-c]quinoline--

Col. 14, line 2, "Found: % C, 67.6; H, 5.4; % N, 26.3." should be --Found: %C, 67.6; %H, 5.4; %N, 26.3.--

Col. 14, line 44, "stirred." should be --stirred,--

Col. 14, line 49, "20° C." should be --20°C slowly, and was then stirred for eighteen hours at 20°C.--

Col. 14, line 54, "1 (2-benzoloxyethyl)" should be --1-(benzoyloxyethyl)--

Col. 15, line 32, "4.1; N," should be --4.1; %N,--

Col. 15, line 46, "0: C, 50.2;" should be --0: %C, 50.2;--

UNITED STATES PATENT AND TRADEMARK OFFICE
CERTIFICATE OF CORRECTION

PATENT NO. : 4,689,338

DATED : August 25, 1987

INVENTOR(S) : John F. Gerster

It is certified that error appears in the above-identified patent and that said Letters Patent is hereby corrected as shown below:

Col. 16, line 3, "% C, 66.3; H, 3.9;" should be --%C, 66.3; %H, 3.9;--

Col. 16, line 8, "to provide" should be --provided--

Col. 16, line 24, "84°-96°C. Recrystallization" should be --84°-96°C. (New Paragraph) Part C (New Paragraph) The product of Part B was reacted with phosphorus oxychloride according to the method of Example 117 to provide 4-chloro-1-(2,3-diacetoxypropyl)-1H-imidazo[4,5-c]-quinoline. (New Paragraph) Part D (New Paragraph) The product of Part C was hydrolyzed according to the method of Example 118 to provide 4-chloro-1-(2,3-dihydroxypropyl)-1H-imidazo[4,5-c]quinoline. Recrystallization--

Col. 16, line 26, "C13H12ClN3O2" should be $C_{13}H_{12}ClN_3O_2$:--

Col. 16, line 27, "4.4; N, 15.1; should be --4.4; %N, 15.1;--

Col. 17, line 18, "78.7; H, 5.1;" should be --78.7; %H, 5.1;--

Col. 17, line 42, "Calculated for $C_{16}H_{19}N_3O_2$% C," should be --Calculated for $C_{16}H_{19}N_3O_2$: %C,--

Col. 17, line 63, "68.2; H, 7.4;" should be --68.2; %H, 7.4;--

Col. 18, line 34, "1-benzyl-4-o" should be --1-benzyl-4---

Col. 18, Line 40, "75.0: %H" should be --75.0; %H--

Col. 19, line 21, "64.6; H, 5.5;" should be --64.6; %H, 5.5;--

Col. 19, line 41, "70.0; H," should be --70.0; %H,--

Col. 19, line 47, "4-(n-hexyl-" should be --4-(n-hexyl)---

UNITED STATES PATENT AND TRADEMARK OFFICE
CERTIFICATE OF CORRECTION

PATENT NO. : 4,689,338            Page 3 of 4

DATED : August 25, 1987

INVENTOR(S) : John F. Gerster

It is certified that error appears in the above-identified patent and that said Letters Patent is hereby corrected as shown below:

Col. 19, line 48, ")amino" should be -- amino--

Col. 19, line 54, "Rf=0.35" should be --$R_f$=0.35--

Col. 20, line 7, "4.5-C]" should be --[4,5-C]--

Col. 20, line 41, "66.8; H," should be --66.8; %H,--

Col. 20, line 43, "6.1:" should be --6.1;--

Col. 20, line 52, "$C_{16}H_{20}N_4$%C," should be --$C_{16}H_{20}N_4$: %C,--

Col. 20, line 53, "71.6; H," should be --71.6; %H,--

Col. 20, line 58, "(Table II)." should be --(Table VII).--

Col. 22, line 8, "Table III." should be --Table VIII.--

Col. 22, Table IX, Ex. No. 161, "1H-4,5-c]" should be --1H-imidazo[4,5-c]--

Col. 23, line 29, "-H-imidazo" should be --1H-imidazo--

Col. 23, line 31, "$C_{19}H_{18}N_4CH_3S_3O_3H$: % C, 0.3;" should be --$C_{19}H_{18}N_4 \cdot CH_3SO_3H$: %C, 60.3;--

Col. 25, line 33, "H, 5.8; % N, 16.0;" should be --%H, 5.8; %N, 16.0;--

Col. 26, line 60, "vI" should be --VI--

UNITED STATES PATENT AND TRADEMARK OFFICE
CERTIFICATE OF CORRECTION

PATENT NO. : 4,689,338

DATED : August 25, 1987

INVENTOR(S) : John F. Gerster

It is certified that error appears in the above-identified patent and that said Letters Patent is hereby corrected as shown below:

Col. 31, line 14, "Dean StCark" should be --Dean Stark--

Col. 33, line 38, Table XIII, "1-amine" should be --4-amine--

Col. 34, line 2, "sufficiCent" should be --sufficient--

Signed and Sealed this

Twenty-seventh Day of December, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,689,338

DATED : August 25, 1987

INVENTOR(S) : John F. Gerster

It is certified that error appears in the above-identified patent and that said Letters Patent is hereby corrected as shown below:

Col. 35, line 1, "1" should read --0--.

Signed and Sealed this

Twenty-eighth Day of November 1995

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO.: 4,689,338

DATED: August 25, 1987

INVENTOR(S): John F. Gerster

It is certified that error appears in the above-identified patent and that said Letters Patent is hereby corrected as shown below:

Col. 35, lines 7-8, claim 3 should read -- A compound according to claim 2, wherein n is the integer 0. --

Signed and Sealed this

Third Day of June, 1997

Attest:

BRUCE LEHMAN

Attesting Officer

Commissioner of Patents and Trademarks